US008658991B2

(12) United States Patent
Pu et al.

(10) Patent No.: US 8,658,991 B2
(45) Date of Patent: Feb. 25, 2014

(54) PARTICLE BEAM IRRADIATION APPARATUS UTILIZED IN MEDICAL FIELD

(75) Inventors: Yuehu Pu, Chiyoda-ku (JP); Katsuhisa Yoshida, Chiyoda-ku (JP); Yuichi Yamamoto, Chiyoda-ku (JP); Hidenobu Sakamoto, Chiyoda-ku (JP); Taizo Honda, Chiyoda-ku (JP); Hisashi Harada, Chiyoda-ku (JP); Takaaki Iwata, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/003,688

(22) PCT Filed: Jun. 3, 2009

(86) PCT No.: PCT/JP2009/060166
§ 371 (c)(1),
(2), (4) Date: Jan. 11, 2011

(87) PCT Pub. No.: WO2010/140236
PCT Pub. Date: Dec. 9, 2010

(65) Prior Publication Data
US 2011/0108737 A1    May 12, 2011

(51) Int. Cl.
*A61N 5/00* (2006.01)
(52) U.S. Cl.
USPC ............... 250/492.1; 250/526; 250/493.1; 250/492.3; 250/396 R
(58) Field of Classification Search
None
See application file for complete search history.

(56) References Cited

U.S. PATENT DOCUMENTS

| 3,736,571 | A | * | 5/1973 | Cohen et al. | 365/114 |
| 3,739,296 | A | * | 6/1973 | Beiser | 372/24 |
| 3,815,094 | A | * | 6/1974 | Smith | 347/121 |
| 4,224,552 | A | * | 9/1980 | Parks | 313/431 |
| 4,295,159 | A | * | 10/1981 | Carollo et al. | 348/761 |

(Continued)

FOREIGN PATENT DOCUMENTS

| EP | 1220585 A1 | 3/2002 |
| EP | 1 220 585 A1 | 7/2002 |

(Continued)

OTHER PUBLICATIONS

Extended European Search Report issued in a corresponding European counterpart application, dated Oct. 1, 2012, 6 pps.

(Continued)

*Primary Examiner* — Andrew Smyth
(74) *Attorney, Agent, or Firm* — Buchanan Ingersoll & Rooney PC

(57) ABSTRACT

In order to obtain a particle beam irradiation apparatus that enlarges the dose distribution of beam spots while suppressing a decrease of the maximum available range of a charged particle beam, the particle beam irradiation apparatus includes a particle beam acceleration means; particle beam transport means; scanning apparatus that includes first scanning means and second scanning means, and two-dimensionally scans the beam; and irradiation control means that controls the scanning apparatus so as to irradiate the beam onto a target region including a plurality of small regions. The irradiation control means controls the first scanning means so as to scan the beam over a small region serving as an irradiation subject among the plurality of the small regions, and controls the second scanning means so as to change the small region serving as the irradiation subject to be a different small region among the plurality of the small regions.

19 Claims, 17 Drawing Sheets

(56) References Cited

U.S. PATENT DOCUMENTS

| | | | |
|---|---|---|---|
| 4,338,548 A * | 7/1982 | Bono et al. | 315/382 |
| 4,467,211 A * | 8/1984 | Smith et al. | 250/492.2 |
| 4,598,415 A * | 7/1986 | Luccio et al. | 378/119 |
| 5,590,169 A * | 12/1996 | Monteiro | 378/87 |
| 6,265,837 B1 * | 7/2001 | Akiyama et al. | 315/503 |
| 6,710,362 B2 * | 3/2004 | Kraft et al. | 250/492.3 |
| 7,482,606 B2 * | 1/2009 | Groezinger et al. | 250/492.3 |
| 2001/0022502 A1 * | 9/2001 | Akiyama et al. | 315/503 |
| 2001/0050338 A1 * | 12/2001 | Nomura | 250/306 |
| 2002/0104970 A1 * | 8/2002 | Winter et al. | 250/400 |
| 2003/0136924 A1 * | 7/2003 | Kraft et al. | 250/492.3 |
| 2004/0104354 A1 | 6/2004 | Haberer | |
| 2004/0140438 A1 * | 7/2004 | Gerlach et al. | 250/492.21 |
| 2006/0033042 A1 * | 2/2006 | Groezinger et al. | 250/492.1 |
| 2008/0006776 A1 * | 1/2008 | Furukawa et al. | 250/396 R |
| 2009/0003524 A1 | 1/2009 | Pu | |
| 2009/0008575 A1 | 1/2009 | Okazaki et al. | |
| 2009/0179656 A1 * | 7/2009 | Mueller et al. | 324/751 |
| 2009/0242789 A1 * | 10/2009 | Tachikawa | 250/396 R |

FOREIGN PATENT DOCUMENTS

| | | | | |
|---|---|---|---|---|
| EP | 1220585 A1 * | 7/2002 | | H05H 3/04 |
| EP | 1477206 A1 * | 11/2004 | | A61N 5/10 |
| EP | 1584353 A1 * | 10/2005 | | A61N 5/10 |
| EP | 1584353 A1 | 12/2005 | | |
| JP | 61-214342 A | 9/1986 | | |
| JP | 03-222320 A | 10/1991 | | |
| JP | 6-154351 A | 6/1994 | | |
| JP | 8-257148 A | 10/1996 | | |
| JP | 08-257148 A | 10/1996 | | |
| JP | 09-159800 A | 6/1997 | | |
| JP | 10-300899 A | 11/1998 | | |
| JP | 11-54405 A | 2/1999 | | |
| JP | 2001-212253 A | 8/2001 | | |
| JP | 2004-358237 A | 12/2004 | | |
| JP | 2005-516634 A | 6/2005 | | |
| JP | 2006-034582 A | 2/2006 | | |
| JP | 2006-166947 A | 6/2006 | | |
| JP | 2006-208200 A | 8/2006 | | |
| JP | 2006208200 A * | 8/2006 | | G21K 5/04 |
| JP | 2006-346120 A | 12/2006 | | |
| JP | 2007-534391 A | 11/2007 | | |
| JP | 2008-279159 A | 11/2008 | | |
| JP | 2009-28500 A | 2/2009 | | |
| JP | 2009-038345 A | 2/2009 | | |
| WO | 0241948 A1 | 5/2002 | | |

OTHER PUBLICATIONS

International Search Report (PCT/ISA/210) issued on Jul. 14, 2009, by Japanese Patent Office as the International Searching Authority for International Application No. PCT/JP2009/060166.

European Search Report in a corresponding EP application dated Jul. 12, 2002, 6 pps.

Office Communication from European Patent Office dated Feb. 26, 2013, issued in corresponding European Patent Application No. 12 168 031.8. (7 pages).

Office Action from the Japan Patent Office dated Aug. 6, 2013, issued in corresponding Japanese Patent Application No. 2010-137241, with a partial English translation thereof. (13 pages).

* cited by examiner

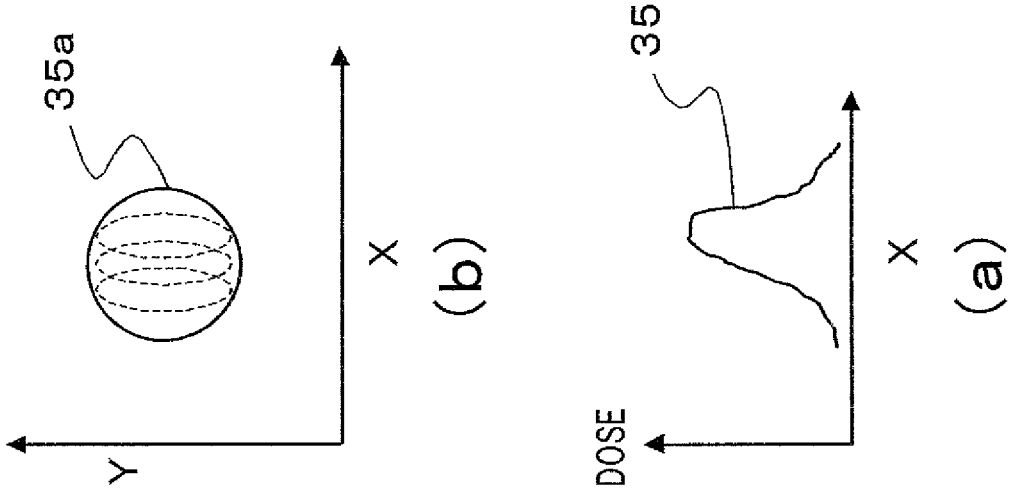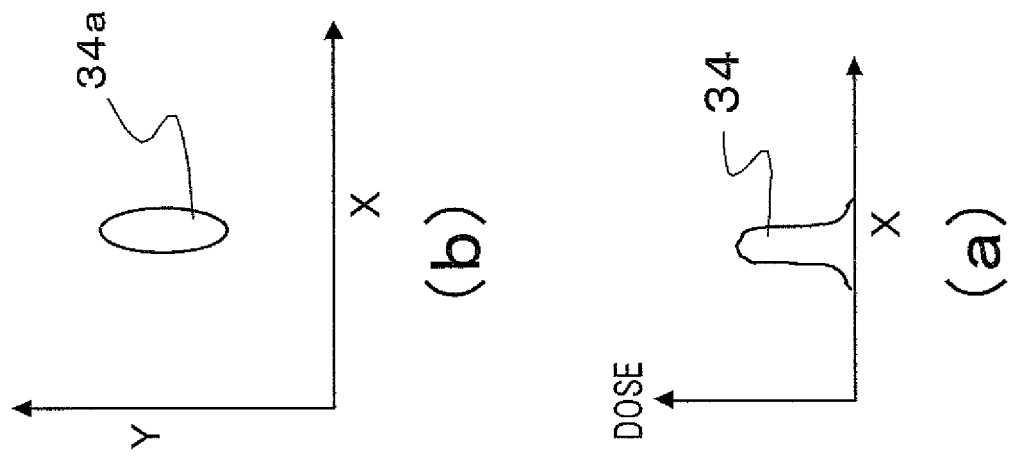

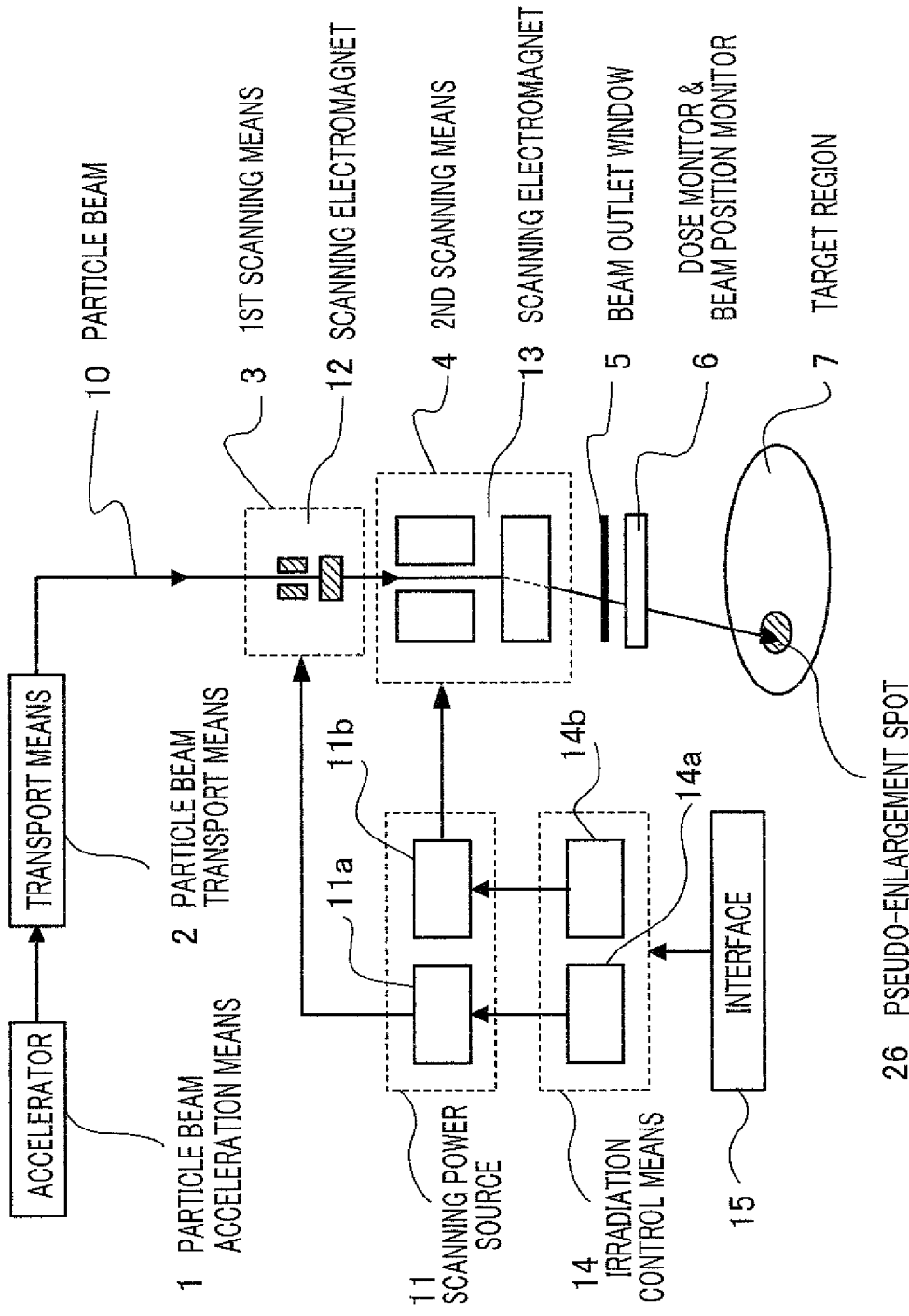

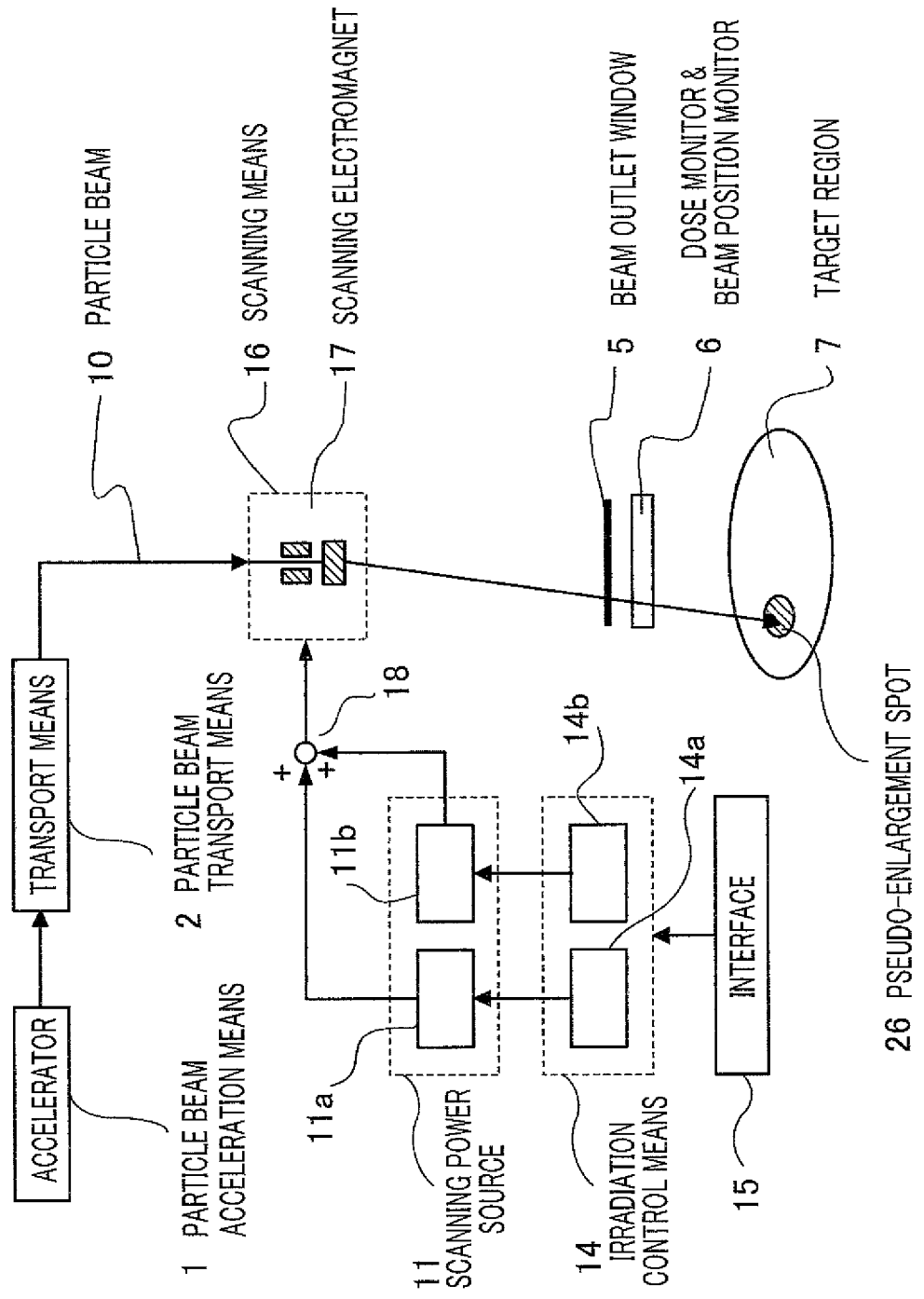

PARTICLE BEAM IRRADIATION APPARATUS UTILIZED IN MEDICAL FIELD

TECHNICAL FIELD

The present invention relates to a particle beam irradiation apparatus utilized in medical field such as cancer treatment and in R&D field.

BACKGROUND ART

A charged particle beam such as a proton or a carbon ion is characterized in that, in the case where it is irradiated inside a body, the intra-body given energy (the amount of absorbed dose) per mass thereof becomes maximum at a position in the vicinity of the range terminal thereof. A particle beam irradiation apparatus utilizes this characteristic to concentrate a dose into a diseased site, so that the effect on the normal tissue around the diseased site can be suppressed to minimum. In general, the transverse cross section of the charged particle beam obtained from an accelerator is a circular or an elliptical shape having a diameter of approximately less than 1 cm. In contrast, in some cases, the size of a diseased site such as a tumor may be ten and several centimeters. Accordingly, as a method of uniformly irradiating a small charged particle beam obtained from an accelerator onto a large diseased site, there exists a so-called "scanning irradiation method" in which a charged particle beam is scanned over the diseased site.

Specifically, control is performed with a scanning electromagnet in such a way that a charged particle beam spot is scanned over the cross section of an irradiation target situated on a plane perpendicular to the irradiation direction of the charged particle beam spot, and the irradiation amount of a charged particle beam is controlled at each of the scanning positions. Eventually, the distribution of the total dose of charged particle beam spots at all scanned positions is made to coincide with the shape of a tumor as much as possible. The scanning of a beam spot in the depth direction is realized by changing the kinetic energy of the charged particle beam. In Patent Document 1, there is described a particle beam therapy system in which, by scanning a charged particle beam in such a way as described above, the three-dimensional distribution of doses is formed in such a way as to coincide with the three-dimensional shape of a diseased site.

In Patent Document 1, there are disclosed an irradiation apparatus and an irradiation method in which a proton beam, accelerated by an accelerator, having beam energy of approximately 200 MeV is formed by a scanning electromagnet in a direction perpendicular to the traveling direction of the beam and in such a way as to have an arbitrary-shape dose distribution. In this case, by changing the energy of a proton beam through insertion of a so-called "range shifter", the proton beam is scanned also in the depth direction. In addition, as may be necessary, the size of a beam spot at an irradiation position is changed by inserting a scattering material such as lead in the irradiation system. The objective of making the size of a beam spot large is to make it possible that a sufficient dose distribution can be formed by less irradiation of beam spots onto a target region of a given size.

PRIOR ART REFERENCE

Patent Document

[Patent Document 1] Japanese Patent Application Laid-Open No. 2001-212253
[Patent Document 2] National Publication of International Patent Application No. 2005-516634

DISCLOSURE OF THE INVENTION

Problems to be Solved by the Invention

As described above, in the conventional particle beam therapy system disclosed in Patent Document 1, the size of a charged particle beam spot utilized for irradiation is changed in accordance with the size of a tumor as the irradiation subject. As the method of changing a spot size, a method of inserting a scattering material such as lead into a beam path is utilized. The beam spot enlargement through insertion of a scattering material is to utilize increase in the angular variance of a beam caused by scattering. However, in the case where a spot size is enlarged through the conventional beam spot changing method, it is required to insert a scattering material of a given thickness; therefore, the maximum range of a charged particle beam is reduced by the amount corresponding to the thickness of the inserted scattering material. Thus, there has been a problem that the maximum beam energy to be utilized for treatment is reduced. In particular, in the case where, as the charged particle beam, a carbon beam is utilized, the carbon beam is heavier than a proton beam and hence less likely to be scattered; therefore, it is required to insert a further thicker scattering material. Thus, there has been a problem that the loss in beam energy caused by insertion of the scattering material becomes larger.

Furthermore, the transverse density distribution (approximately proportional to the dose distribution formed by spots) of enlarged spots obtained by insertion of a scattering material generally has a distribution close to a Gaussian distribution; assuming that the standard deviation in the distribution of the enlarged spots is $\sigma 1$, the 80%-to-20% width (hereinafter, referred to as a penumbra), which denotes the edge-portion steepness of a dose distribution formed by scanning the enlarged spots over a tumor region, is at least $1.12 \times \sigma 1$. In other words, the gradient of the final dose distribution to be obtained, which is proportional to $\sigma 1$, becomes large. In general, in a therapy utilizing a particle beam, the smaller is the penumbra of the formed dose distribution, the smaller becomes an unnecessary dose to be irradiated onto a normal tissue other than a tumor as the irradiation target. Accordingly, there has been a problem that the penumbra of the dose distribution formed by spots obtained through the conventional spot size enlargement method increases in proportion to the spot size $\sigma 1$ and hence there increases an unnecessary dose to be irradiated onto a normal tissue in the vicinity of a tumor.

Patent Document 2 discloses a method in which there is changed setting of a quadrupole electromagnet and the like provided in a beam transport system so that the spot size of a beam utilized for irradiation is changed. In this case, not only there has been a problem that, because it is required to change the setting of almost all electromagnets in the beam transport system, an irradiation control means becomes troublesome, but also there has been a problem that the maximum spot size that can be obtained through the setting change is limited by the size of a gap of the electromagnet in the beam transport system.

The present invention has been implemented in order to solve the foregoing problems; the first objective thereof is to provide a particle beam irradiation apparatus that enlarges the dose distribution of beam spots, while suppressing the maximum available range of a charged particle beam from decreasing. The second objective of the present invention is to provide a beam spot dose distribution changing means that can suppress the penumbra of a dose distribution formed through scanning irradiation from increasing.

Means for Solving the Problems

A particle beam irradiation apparatus according to the present invention is provided with a particle beam acceleration means that accelerates a charged particle beam; a particle beam transport means that transports a charged particle beam launched from the particle beam acceleration means; a scanning apparatus that includes a first scanning means and a second scanning means, both of which generate a deflection magnetic field or a deflection electric field in directions that are perpendicular to a traveling direction of the charged particle beam, and two-dimensionally scans the charged particle beam transported by the particle beam transport means; and an irradiation control means that controls the scanning apparatus so as to irradiate the charged particle beam onto a target region including a plurality of small regions. The irradiation control means controls the first scanning means so as to scan the charged particle beam over a small region serving as an irradiation subject among the plurality of the small regions, and controls the second scanning means so as to change the small region serving as the irradiation subject to be a different small region among the plurality of the small regions.

Moreover, a particle beam irradiation apparatus according to the present invention is provided with a particle beam acceleration means that accelerates a charged particle beam; a particle beam transport means that transports a charged particle beam launched from the particle beam acceleration means; a scanning apparatus that generates a deflection magnetic field or a deflection electric field in directions that are perpendicular to a traveling direction of the charged particle beam, and two-dimensionally scans the charged particle beam transported by the particle beam transport means; and an irradiation control means that controls the scanning apparatus so as to irradiate the charged particle beam onto a target region including a plurality of small regions. The irradiation control means outputs to the irradiation apparatus a first control signal for controlling the scanning apparatus so as to scan the charged particle beam over a small region serving as an irradiation subject among the plurality of the small regions, and a second control signal for controlling the scanning apparatus so as to change the small region serving as the irradiation subject to be a different small region among the plurality of the small regions.

Advantage of the Invention

In a particle beam irradiation apparatus according to the present invention, the enlargement of a beam spot is realized by use of the scanning apparatus; therefore, unnecessary loss in the beam energy can be eliminated. Accordingly, compared with a conventional particle beam irradiation apparatus whose particle beam acceleration means has the same maximum exiting beam energy, the particle beam irradiation apparatus according to the present invention can perform irradiation onto a target region situated at a deeper position.

Moreover, because the size of a spot can be enlarged by use of an irradiation apparatus, the standard deviation $\sigma 1$ of the dose distributions of spots included in a pseudo-enlargement spot (small region) is kept approximately the same as the standard deviation $\sigma 1$ at a time when the spot size has not been enlarged. Accordingly, the penumbra, of the dose distribution of pseudo-enlargement spots, which is in proportion to the standard deviation $\sigma 1$ does not become large; thus, an unnecessary dose irradiated onto a normal tissue in the vicinity of a tumor can be minimized.

Further, a sufficient dose distribution can be formed by less irradiation of beam spots onto a target region of the same size; therefore, time and effort of irradiation control can be reduced.

BRIEF DESCRIPTION OF THE DRAWINGS

FIG. 14 is a set of charts representing the dose distribution of pre-enlargement spots obtained from an accelerator and the shape thereof;

FIG. 15 is a set of charts representing a dose distribution of pseudo-enlargement spots and the shape thereof according to Embodiment 3;

FIG. 16 is a configuration diagram illustrating a particle beam irradiation apparatus according to Embodiment 5;

FIG. 17 is a configuration diagram illustrating a particle beam irradiation apparatus according to Embodiment 6.

BEST MODE FOR CARRYING OUT THE INVENTION

Embodiment 1

Figure 1:
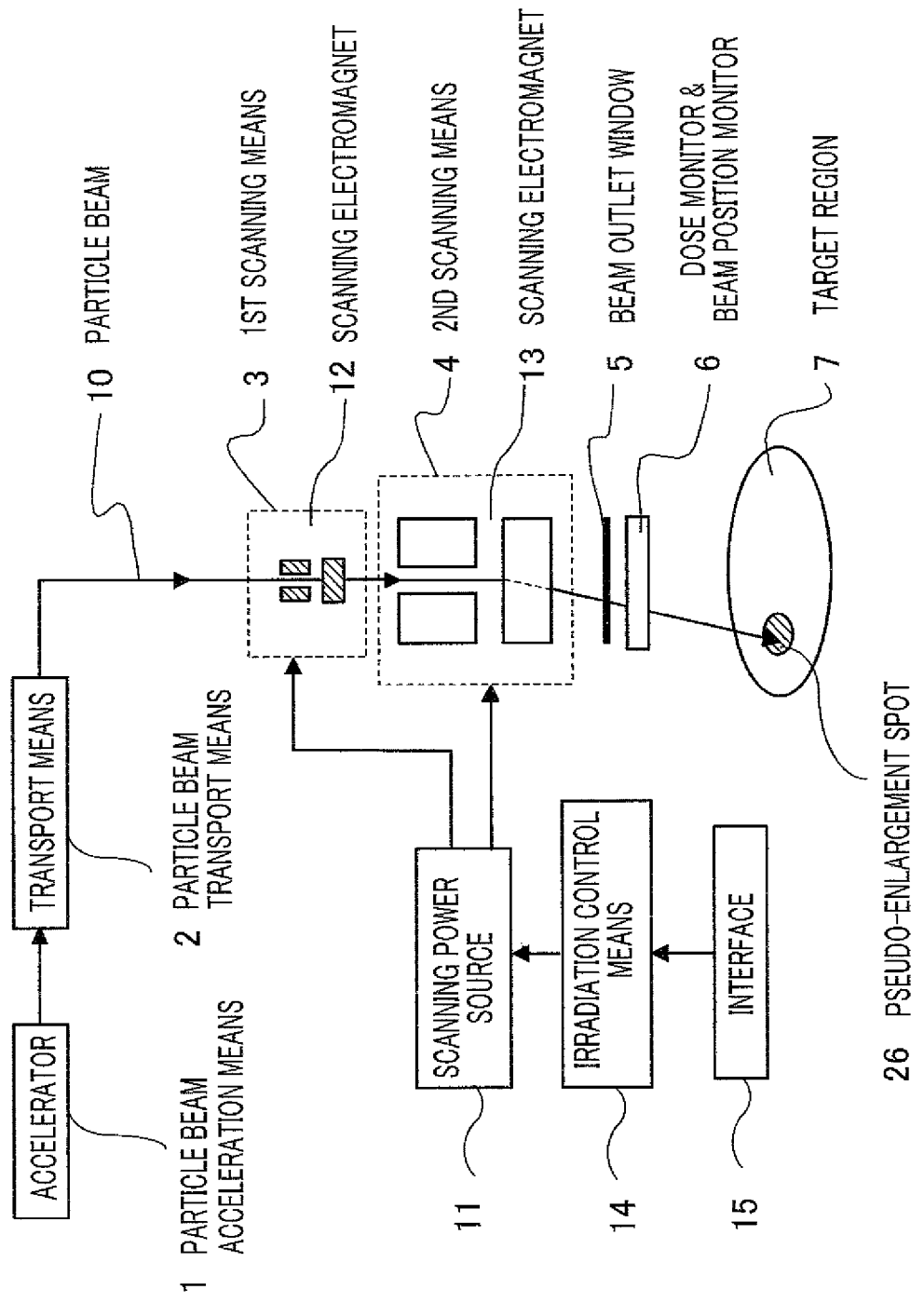
FIG. 1 is a configuration diagram illustrating a particle beam irradiation apparatus according to Embodiment 1 of the present invention.

FIG. 1 is a configuration diagram illustrating a particle beam irradiation apparatus according to Embodiment 1 of the present invention. In FIG. 1, reference numeral 1 denotes a particle beam acceleration means that accelerates an incident charged particle beam; reference numeral 2 denotes a particle beam transport means that transports a charged particle beam that has been accelerated and launched; reference numeral 3 denotes a first scanning means having a charged particle beam scanning electromagnet 12; reference numeral 4 denotes a second scanning means having a charged particle beam scanning electromagnet 13; electric power is applied from a scanning power source 11 to the charged particle beam scanning electromagnets 12 and 13 so that scanning is performed. The first scanning means 3, the second scanning means 4, and the scanning power source 11 configure a scanning apparatus. In FIG. 1, the scanning apparatus is disposed at the downstream side of the particle beam transport means 2 in a charged particle beam path. Reference numeral 5 denotes a beam outlet window; reference numeral 6 denotes a set of a dose monitor for a charged particle beam and a beam position monitor; reference numeral 7 denotes a target region, which is an irradiation subject. Reference numeral 14 denotes an irradiation control means that controls the whole particle beam irradiation apparatus; the irradiation control means controls the energy of a beam from the accelerator 1, the launch and stoppage of a charged particle beam, and irradiation onto the target region. Reference numeral 15 denotes an interface that can be operated by an operator and inputs a command to the irradiation control means 14; the interface is configured with a display device, a keyboard, and the like. Reference numeral 10 denotes a charged particle beam that is accelerated by the accelerator 1 to a point that it has predetermined energy and then is transported by the particle beam transport means 2 to the scanning apparatus. Reference numeral 26 denotes a pseudo-enlargement spot whose irradiation region has been enlarged by the first scanning means. In addition, the beam outlet window 5 may be disposed at the upstream side of the second scanning means 4 or the first scanning means 3. The set 6 of a dose monitor and a beam position monitor may be disposed at the upstream side of the second scanning means 4.

Figure 3:
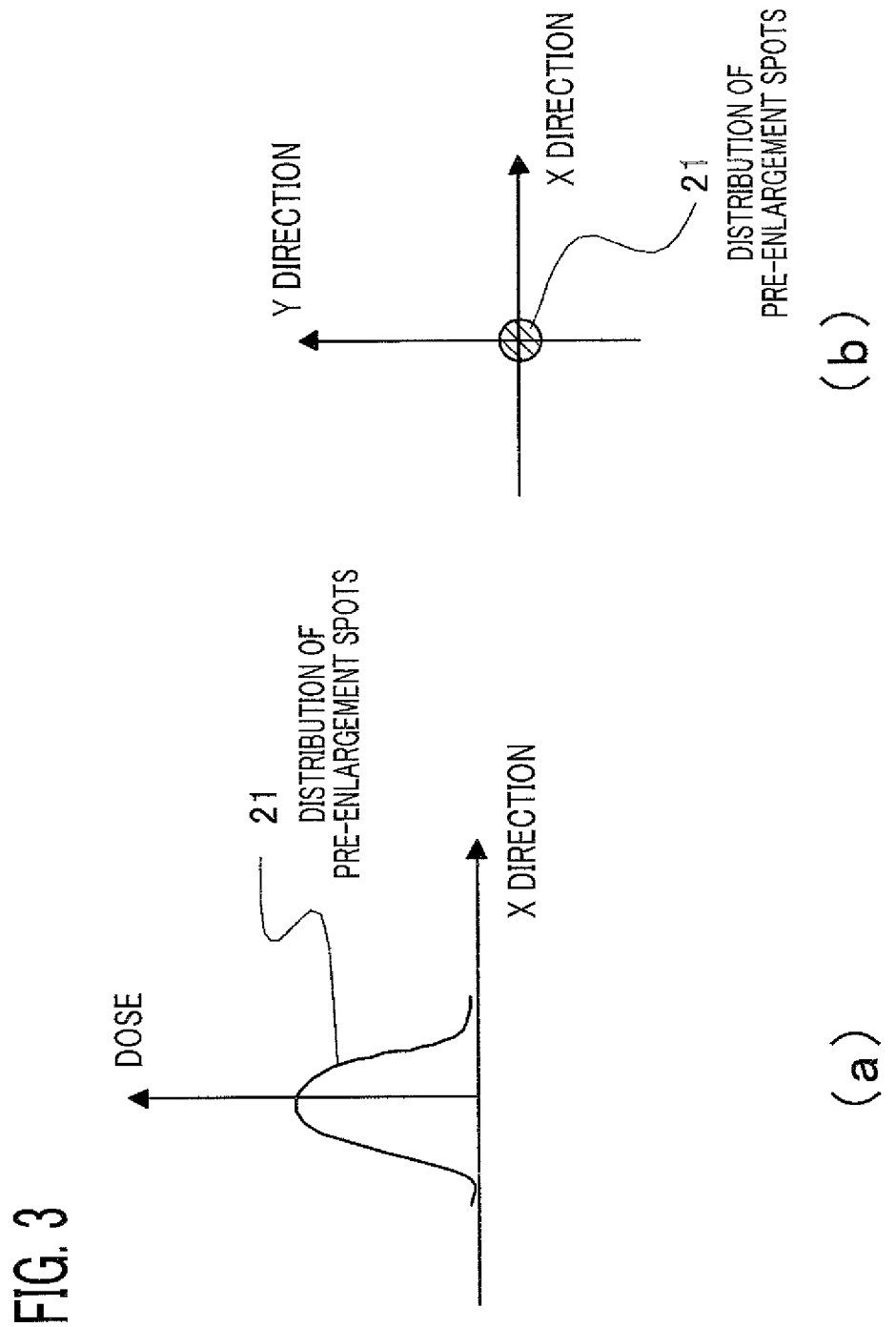
FIG. 3 is a set of charts for explaining the dose distribution of pre-enlargement charged particle beam spots according to Embodiment 1.

FIG. 3 is a set of charts for explaining the dose distribution of pre-enlargement charged particle beam spots and the spot position thereof in the target region 7, according to Embodiment 1. In FIG. 3(a), reference numeral 21 denotes the dose distribution, in the target region 7, of pre-enlargement charged particle beam spots; in FIG. 3(b), the spot position is represented. Hereinafter, in the target region 7, the depth direction is referred to as the "Z direction", and directions perpendicular to the Z direction are referred to as the "X direction" and the "Y direction".

Figure 4:
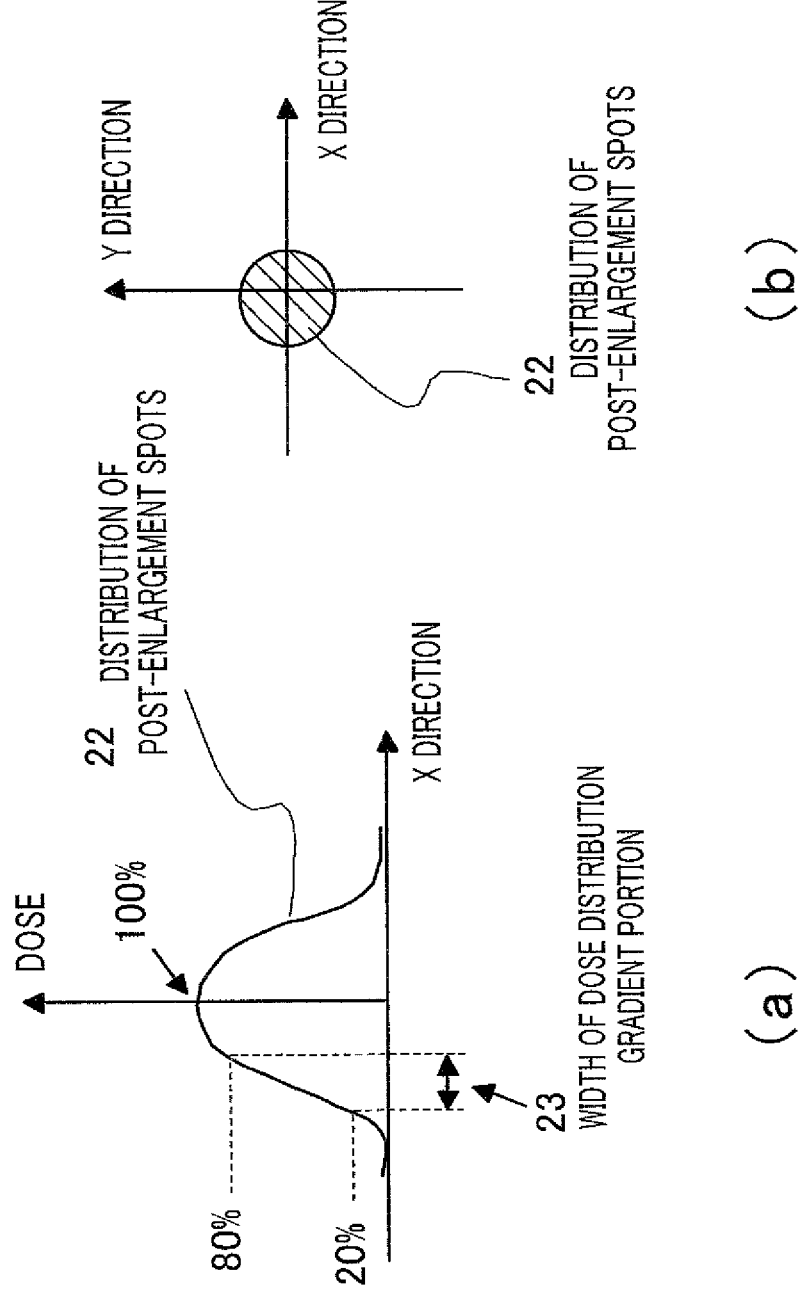
FIG. 4 is a set of charts for explaining the dose distribution of post-enlargement charged particle beam spots according to a conventional technology.

FIG. 4 is a set of charts for explaining the dose distribution of post-enlargement charged particle beam spots in the case where a scatterer according to a conventional technology is inserted. In FIG. 4(a), reference numeral 22 denotes the dose distribution, in the target region 7, of charged particle beam spots enlarged through insertion of a scatterer; in FIG. 4(b), the spot position is represented. Reference numeral 23 denotes the width of a dose distribution gradient portion and referred to as a dose distribution penumbra.

Figure 5:
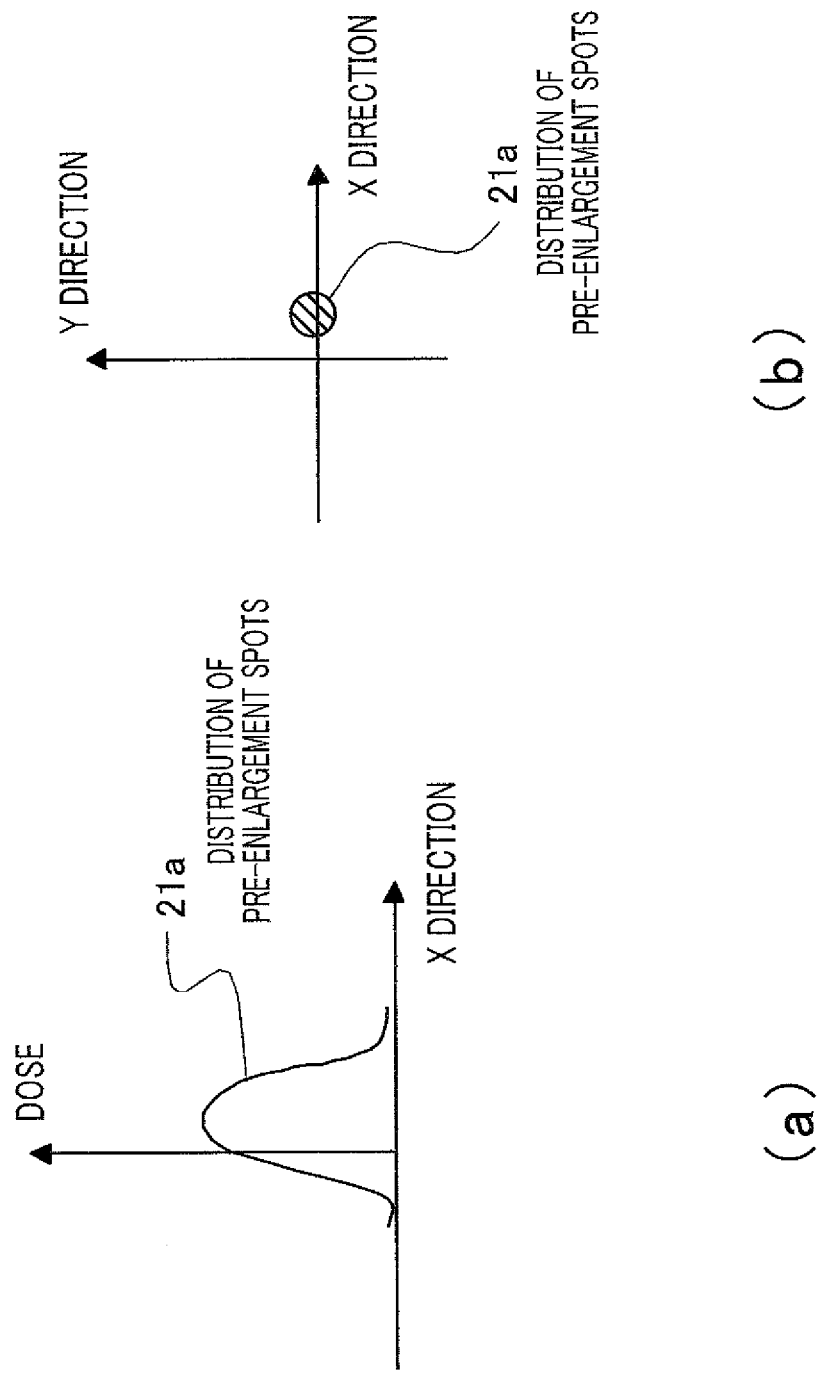
FIG. 5 is a set of charts for explaining the principle of enlargement, of a charged particle beam spot, by a first scanning means according to Embodiment 1.
Figure 6:
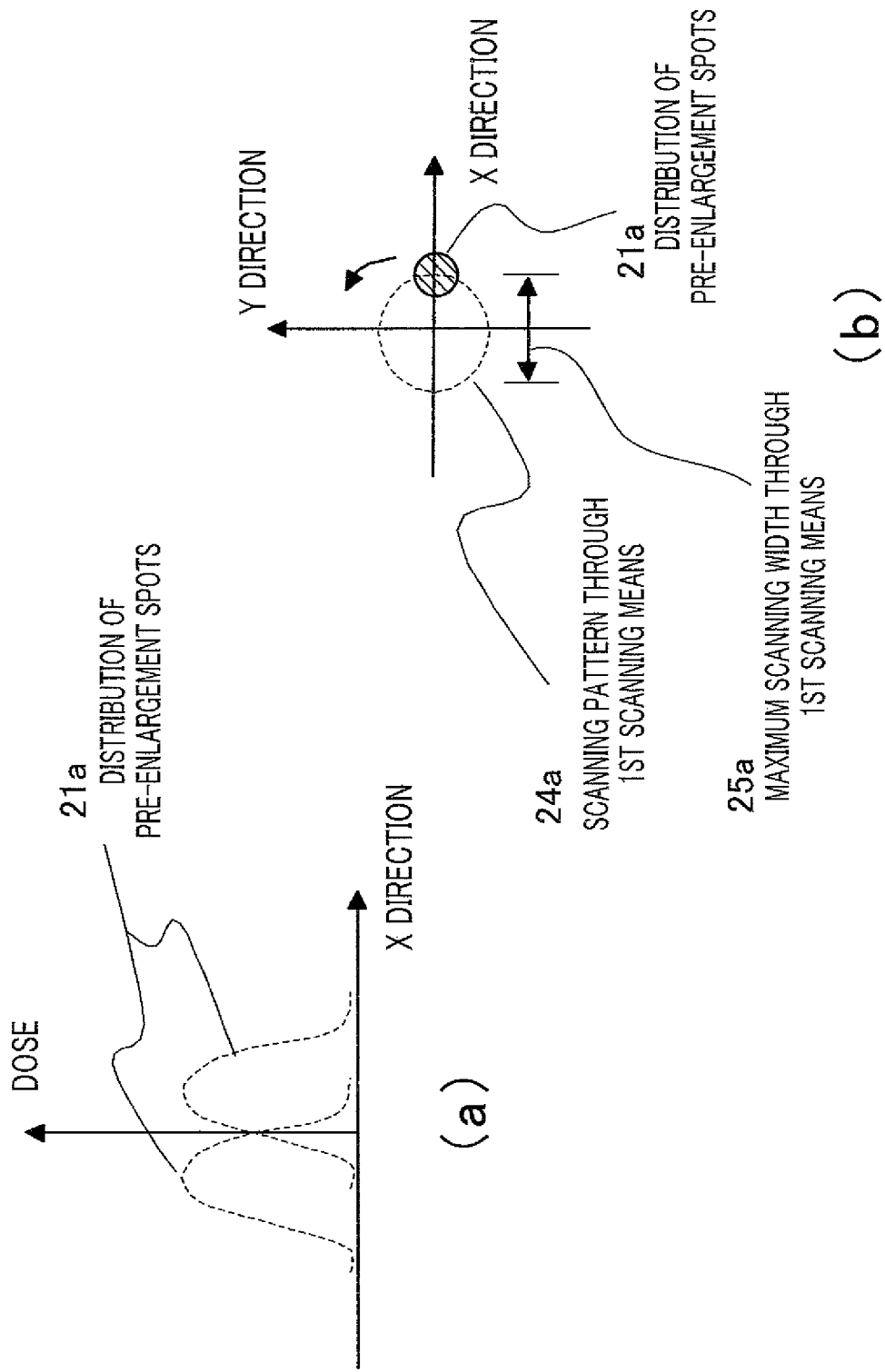
FIG. 6 is a set of charts for explaining the principle of enlargement, of a charged particle beam spot, by a first scanning means according to Embodiment 1, and represents the appearance of a pre-enlargement spot being scanned.

FIG. 5 is a set of charts for explaining the dose distribution of pre-enlargement charged particle beam spots and the spot position thereof, in the target region 7, according to Embodiment 1; FIG. 5 is a set of charts also for explaining the principle of enlargement, of a charged particle beam spot, by the first scanning means 3. In FIG. 5(a), reference numeral 21a denotes the dose distribution, in the target region 7, of pre-enlargement charged particle beam spots; in FIG. 5(b), the spot position is represented. FIG. 6 is a set of charts for explaining the principle of enlargement, of a charged particle beam spot, by the first scanning means 3 according to Embodiment 1, and represents the appearance of a pre-enlargement spot 21a being scanned. In FIG. 6(a), reference numeral 21a similarly denotes the dose distribution of pre-enlargement charged particle beam spots; in FIG. 6(b), the spot position is represented. Reference numeral 24a indicates an example of pattern of scanning performed by the first scanning means 3. Reference numeral 25a indicates an example of maximum scanning width formed by the first scanning means 3.

Figure 7:
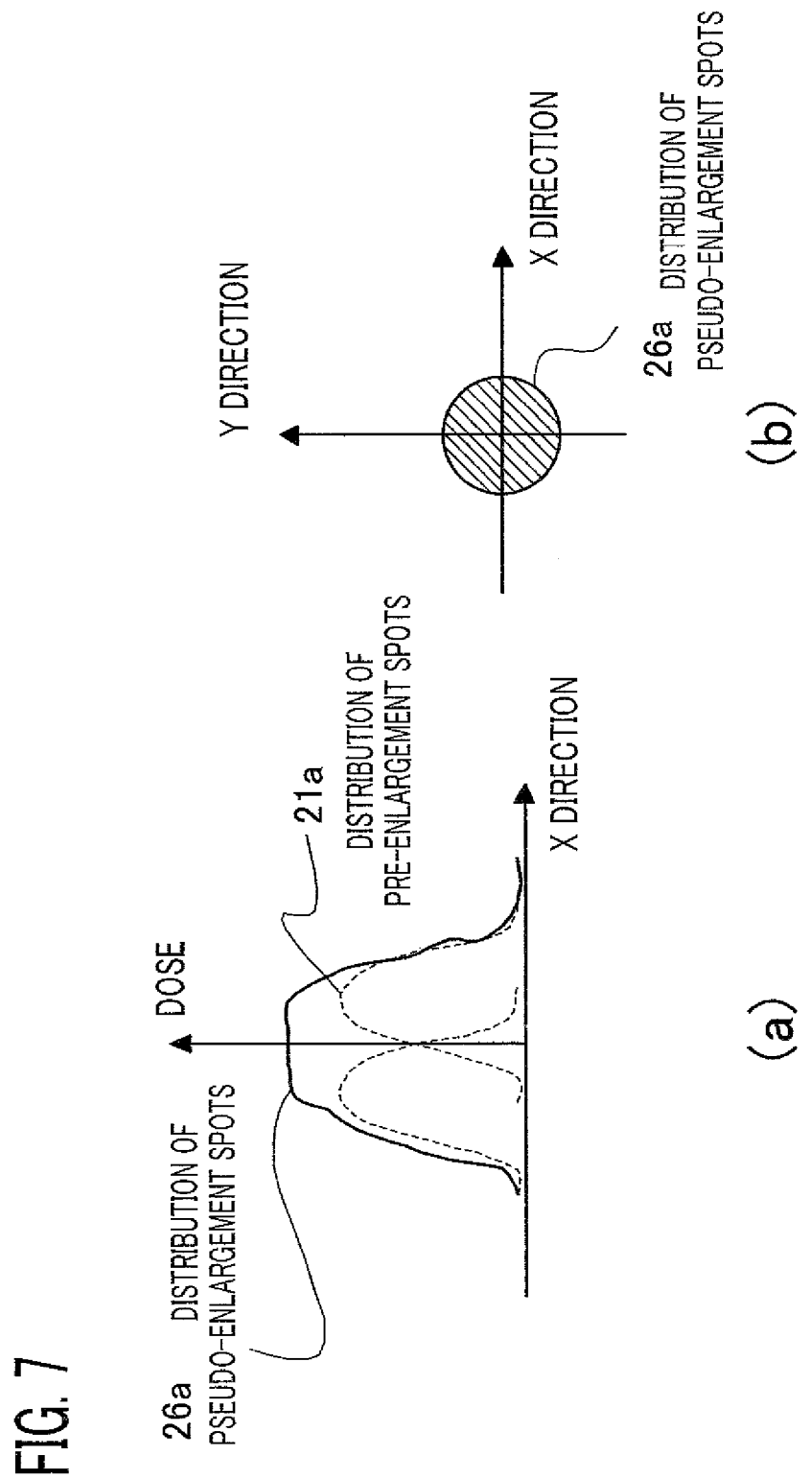
FIG. 7 is a set of charts for explaining the dose distribution of pseudo-enlargement spots enlarged by the first scanning means and the spot position according to Embodiment 1.

FIG. 7 is a set of charts for explaining the dose distribution of post-enlargement charged particle beam spots, which is formed through high-speed scanning performed by the first scanning means 3 in accordance with the first scanning pattern 24a represented in FIG. 6, and the spot position thereof. With regard to FIG. 7, in FIG. 7(a), reference numeral 26a denotes the dose distribution of post-enlargement charged particle beam spots (pseudo-enlargement spots); in FIG. 7(b), the spot position is represented.

Figure 8:
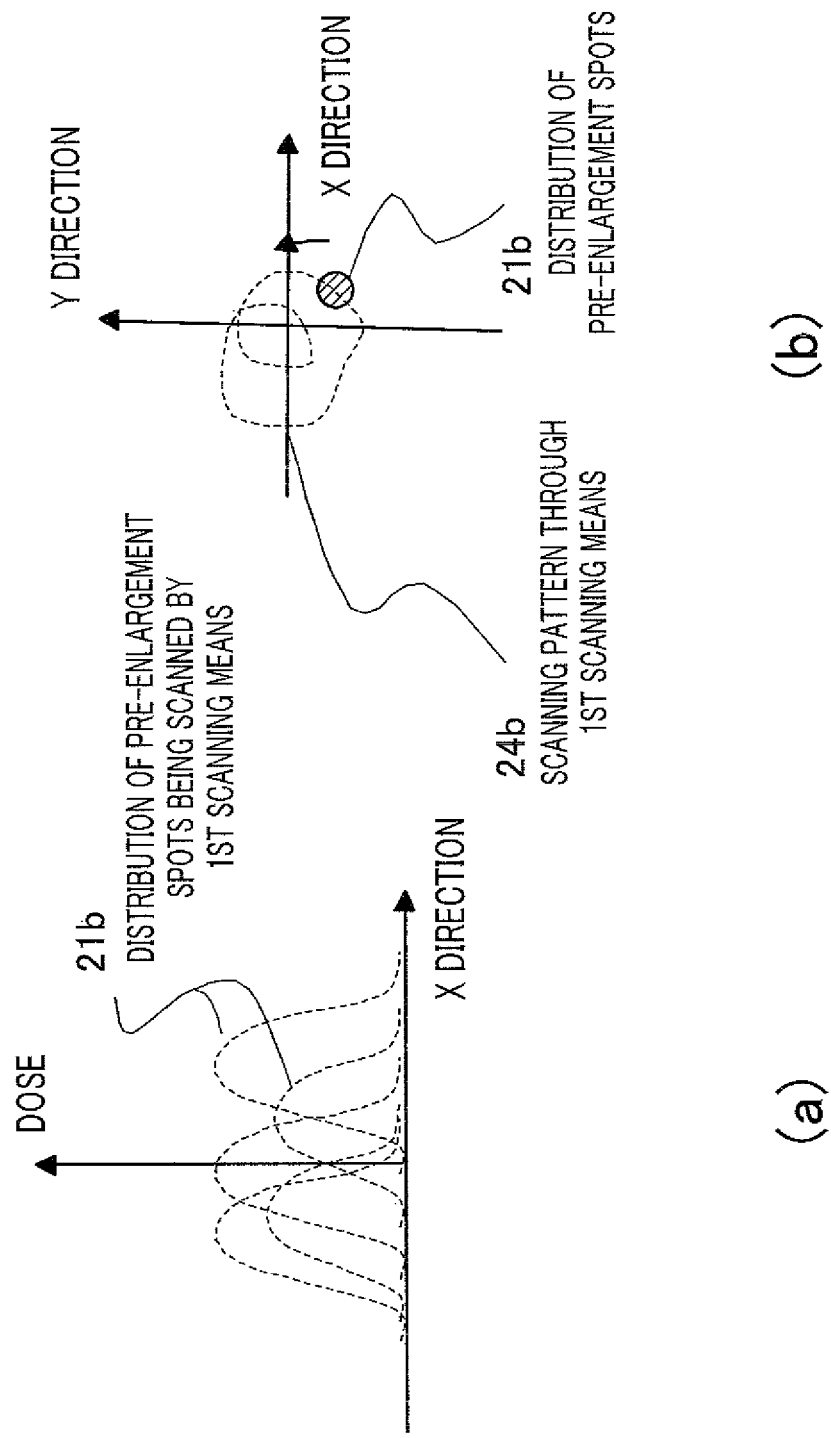
FIG. 8 is a set of charts for explaining the principle of enlargement, of another charged particle beam spot, by the first scanning means according to Embodiment 1, and represents the appearance of a pre-enlargement spot being scanned.
Figure 9:
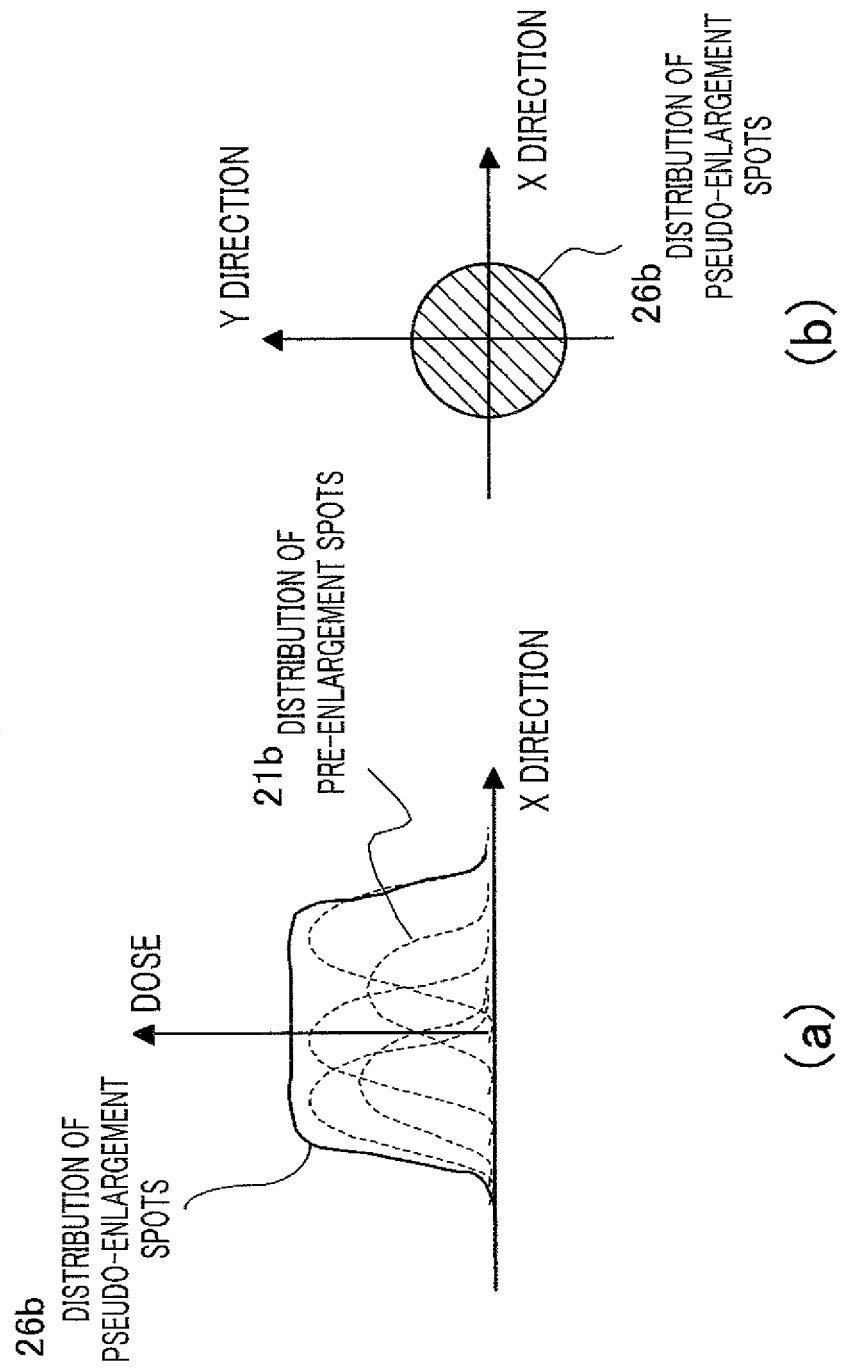
FIG. 9 is a set of charts for explaining the dose distribution of other pseudo-enlargement spots enlarged by the first scanning means and the spot position according to Embodiment 1.

FIG. 8 is a set of charts for explaining the principle of enlargement, of a charged particle beam spot, by the first scanning means 3 according to Embodiment 1, and represents the appearance of another pre-enlargement spot 21b being scanned in accordance with another first scanning pattern 24b. With regard to FIG. 8, in FIG. 8(a), reference numeral 21b similarly denotes the dose distribution of pre-enlargement charged particle beam spots; in FIG. 8(b), the spot position is represented. FIG. 9 is a set of charts for explaining the dose distribution of post-enlargement charged particle beam spots (pseudo-enlargement spots), which is formed through high-speed scanning performed by the first scanning means 3 in accordance with the scanning pattern 24b represented in FIG. 8, and the spot position thereof. In FIG. 9(a), reference numeral 21b denotes the dose distribution of pre-enlargement spots, and reference numeral 26b denotes the dose distribution of post-enlargement charged particle beam spots (pseudo-enlargement spots); in FIG. 9(b), the spot position is represented.

Figure 10:
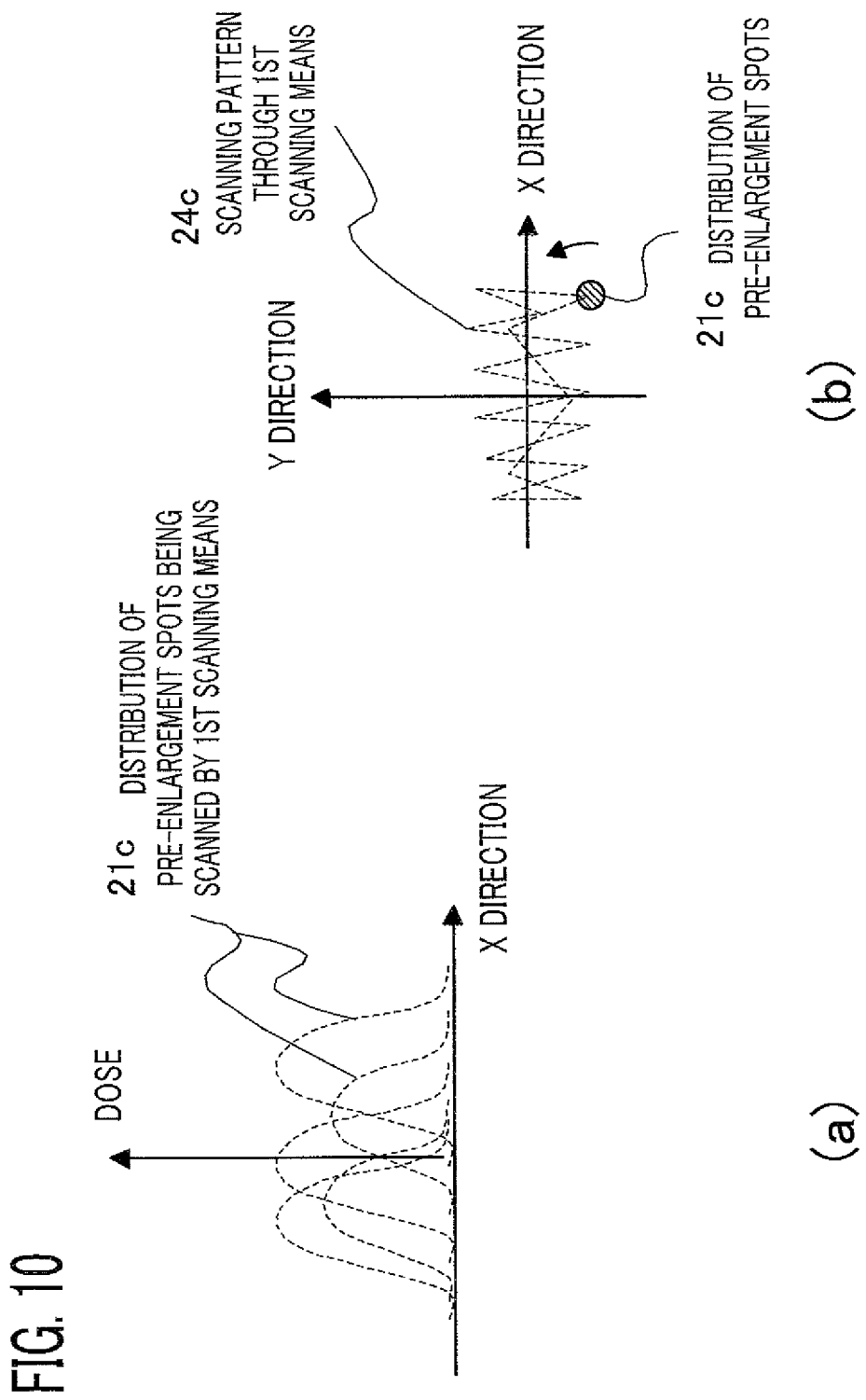
FIG. 10 is a set of charts for explaining the principle of enlargement, of further another charged particle beam spot, by the first scanning means according to Embodiment 1, and represents the appearance of a pre-enlargement spot being scanned.
Figure 11:
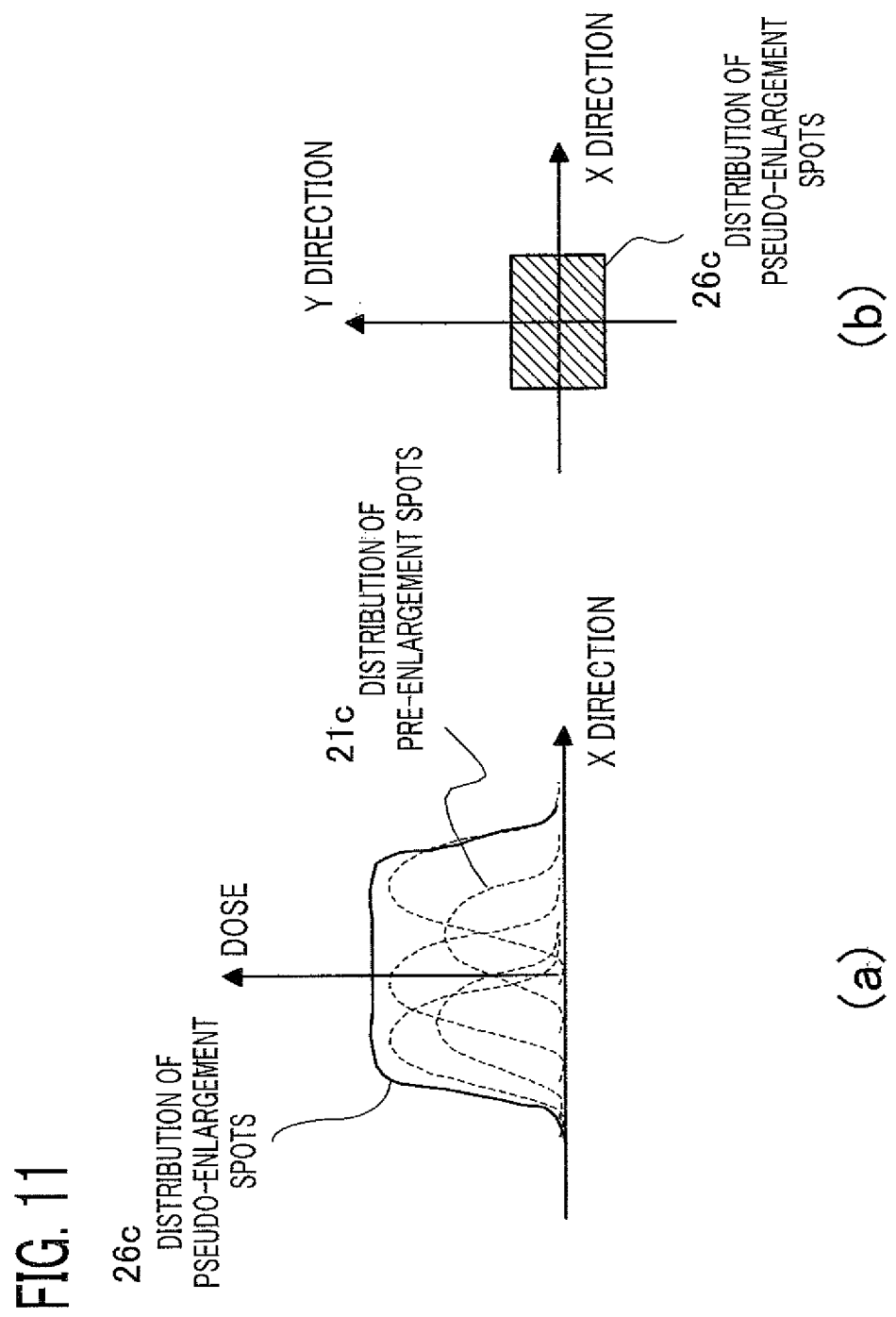
FIG. 11 is a set of charts for explaining the dose distribution of further other pseudo-enlargement spots enlarged by the first scanning means and the spot position according to Embodiment 1.

FIG. 10 is a set of charts for explaining the principle of enlargement, of a charged particle beam spot, by the first scanning means 3 according to Embodiment 1, and represents the appearance of another pre-enlargement spot 21c being scanned in accordance with further another first scanning pattern 24c. In FIG. 10(a), reference numeral 21c similarly denotes the dose distribution of pre-enlargement charged particle beam spots; in FIG. 10(b), the spot position is represented. FIG. 11 is a set of charts for explaining the dose distribution of pseudo-enlargement spots, which is formed through high-speed scanning performed by the first scanning means 3 in accordance with the scanning pattern 24c represented in FIG. 10, and the spot position thereof. In FIG. 11(a), reference numeral 21c denotes the dose distribution of pre-enlargement spots, and reference numeral 26c denotes the dose distribution of pseudo-enlargement spots; in FIG. 11(b), the spot position is represented. The scanning patterns 24a, 24b, and 24c formed by the first scanning means and the combination among them are preliminarily set through a treatment plan; however, a command may be inputted to the irradiation control means 14 through the interface 15 so that selection can be performed.

Figure 12:
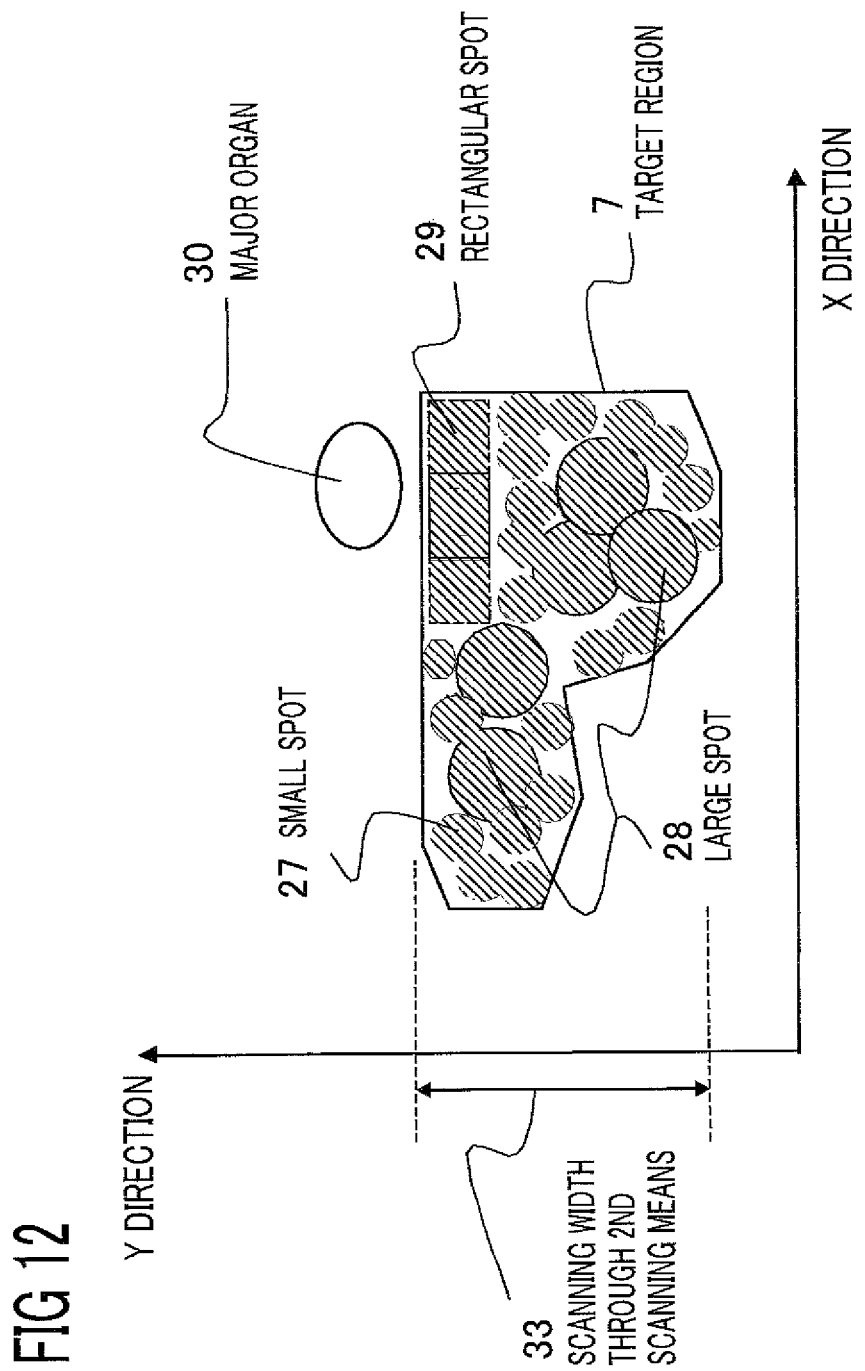
FIG. 12 is a conceptual chart representing the situation in which, by use of a second scanning means according to Embodiment 1, various kinds of beam spots enlarged by the first scanning means are scanned so that a predetermined dose distribution is formed in a diseased site.

FIG. 12 is a chart representing the relationship between the positions of enlarged spots (pseudo-enlargement spots) and the target region, in the case where, in Embodiment 1, the second scanning means 4 scans beam spots, having various dose distributions, of charged particle beams (pseudo-enlargement spots) enlarged by the first scanning means 3 so that a predetermined second scanning pattern is formed in the target region 7. In FIG. 12, reference numeral 27 denotes an example where the size of the pseudo-enlargement spot (small region) 26 is small; reference numeral 28 denotes an example where the size of the pseudo-enlargement spot (small region) 26 is large; reference numeral 29 denotes an example where the shape of a pseudo-enlargement spot (small region) is quadrangular. Reference numeral 30 denotes a major organ that is situated in the vicinity of the target region 7 and the irradiation dose onto which should be reduced as much as possible. Reference numeral 33 denotes a scanning width formed by the second scanning means 4.

In order to form the predetermined second scanning pattern in the target region 7 represented in FIG. 12, it may be allowed that each of the pseudo-enlargement spots (i.e., the small spot, the large spot, and the quadrangular spot) is formed through continuous scanning by the first scanning means 3, and that the predetermined second scanning pattern is formed through continuous scanning (raster scanning), discontinuous (spot scanning), or continuity-discontinuity mixed scanning (hybrid scanning) by the second scanning means 4. Accordingly, it may be allowed that, after controlling the first scanning means 3 so that a pseudo-enlargement spot is formed from a charged particle beam, the irradiation control means 14 controls the second scanning means 4 so that the scanning is performed over the position of the pseudo-enlargement spot. Moreover, it maybe allowed that, while controlling the first scanning means 3 so that a pseudo-enlargement spot is formed from a charged particle beam, the irradiation control means 14 controls the second scanning means 4 so that the scanning is performed over the position of the pseudo-enlargement spot.

Figure 13:
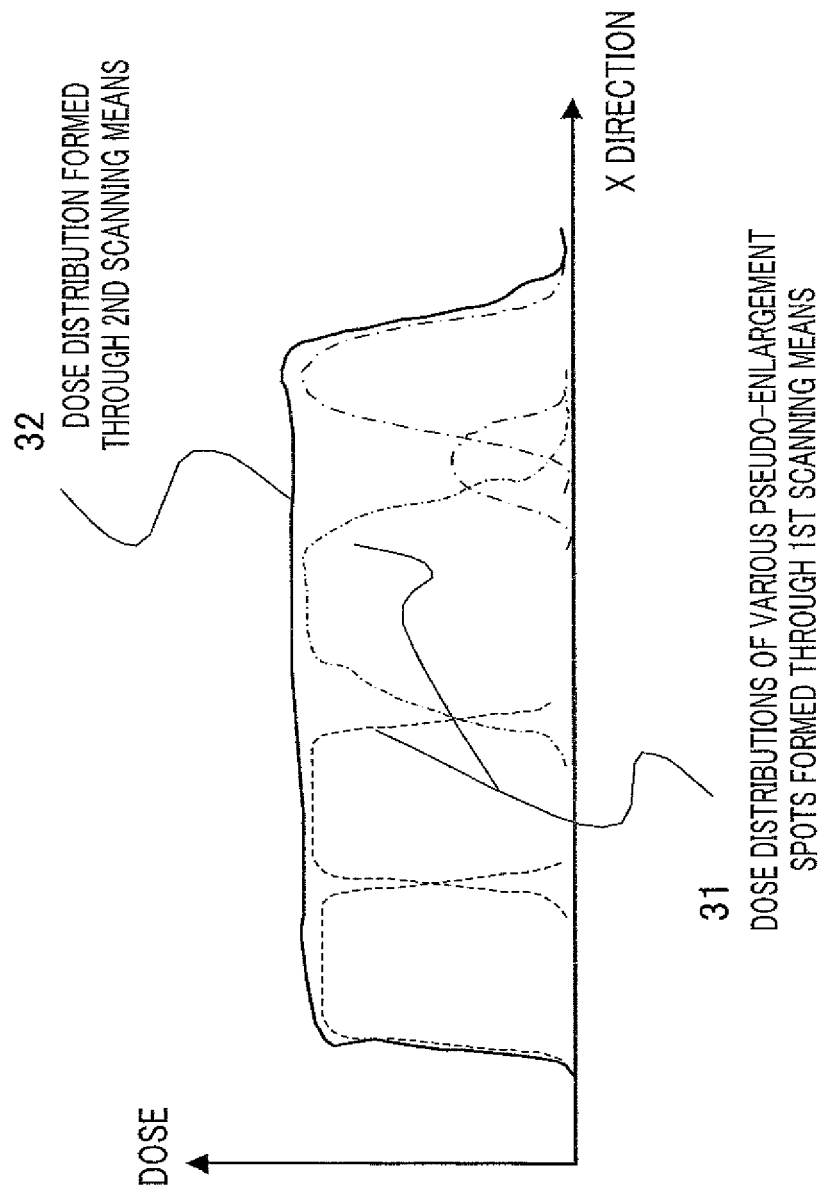
FIG. 13 is a conceptual chart representing the situation in which, by use of a second scanning means according to Embodiment 1, various kinds of beam spots enlarged by the first scanning means are scanned so that a predetermined dose distribution is formed in a diseased site.

FIG. 13 is a chart representing the final dose distribution (the dose distribution obtained through combining all of the dose distributions of irradiated pseudo-enlargement spots) obtained in the case where, in Embodiment 1, the second scanning means 4 scans beam spots, having various dose distributions, of charged particle beams enlarged by the first scanning means 3 so that the predetermined second scanning pattern is formed in the target region 7. In FIG. 13, reference numeral 31 denotes the respective dose distributions of various pseudo-enlargement spots formed by the first scanning means 3. Reference numeral 32 denotes the final combined dose distribution formed by the second scanning means 4.

Next, the basic configuration and the operation of a particle beam irradiation apparatus (or a particle beam therapy system) according to Embodiment 1 will be explained. In FIG. 1, after accelerating an incident charged particle beam to a point that it has beam energy required for therapy, the particle beam acceleration means 1 configured with a particle beam accelerator and the like launches the charged particle beam. The particle beam transport means 2 transports the launched charged particle beam from the accelerator chamber to the irradiation chamber provided with the first scanning means 3, the second scanning means 4, the beam outlet window 5 for extracting a beam from the vacuum duct, and the set 6 of the dose monitor for managing the dose of each spot and the beam position monitor for managing spot positions.

The first scanning means 3 is configured, for example, with two high-speed scanning electromagnets whose charged-particle-beam deflection directions, which are each perpendicular to the traveling direction of a beam, are perpendicular to each other. The second scanning means 4 is configured in such a way as to be separated and independent from the first scanning means 3; for example, it is configured with two scanning electromagnets whose charged-particle-beam deflection directions, which are each perpendicular to the traveling direction of a beam, are perpendicular to each other. In this regard, however, the scanning speed f1 (the scanning cyclic frequency f1) of the first scanning means 3 is faster (higher, in terms of the frequency) than the scanning speed f2 (the scanning cyclic frequency f2) of the second scanning means 4. The scanning width A1 (the scanning range in the target region 7) of the first scanning means 3 is smaller than the scanning width A2 (the scanning range in the target region 7) of the second scanning means 4. Firstly, the charged particle beam 10 that has been transported to the irradiation chamber is rapidly scanned by the first scanning means 3 in accordance with the first scanning patterns 24a, 24b, and 24c preliminarily set in a treatment plan (unillustrated), so that there is formed a pseudo-enlargement spot that is distributed in a pseudo manner over a range wider than the original beam spot.

FIGS. 6 and 7 each represent formation of the dose distribution of pseudo-enlargement spots in the case where the first scanning pattern 24a is a circular orbit. In this example, the pre-enlargement spot 21a is scanned by the first scanning means 3 in such a way as to draw a circular orbit having as large a radius as the beam diameter of the pre-enlargement spot 21a, in accordance with the first scanning pattern 24a represented in FIG. 6. As a result, there is obtained the dose distribution 26a of pseudo-enlargement spots represented in FIG. 7. In addition, because the scanning width 25a required by the first scanning means 3 is large enough when it is approximately as large as the original spot size, the required scanning magnetic field may be small; therefore, scanning can be performed at extremely high speed.

With regard to the dose distribution 26a of pseudo-enlargement spots represented in FIG. 7, the standard deviation σ1, in the dose distribution, of spots that form the sizes of the pseudo-enlargement spots is kept to be the same value as when the spot size has not been enlarged. Accordingly, the penumbra, of the dose distribution 26a of pseudo-enlargement spots, which is in proportion to the standard deviation σ1 does not become large. Even in the case where the beam current of the charged particle beam 10 launched from the particle beam acceleration means 1 changes with time, the formed dose distribution 26a of pseudo-enlargement spots can be kept approximately constant, by making the scanning period (cyclic time of the first scanning pattern) of the first scanning means 3 sufficiently short compared with the scale of the temporal change in the beam current. In the case where the beam current of the charged particle beam 10 is approximately constant with respect to time, the scanning speed of the first scanning means 3 need not to be extremely high; it is only necessary that the scanning speed is high enough compared with the scanning speed of the second scanning means 4. In contrast, with regard to a spot to be irradiated onto the middle region of an irradiation field, by performing irradiation intentionally by use of a large-penumbra pseudo-enlargement spot, there can be demonstrated an effect that the error, in the final dose distribution, caused by the positional fluctuation of a spot to be irradiated can be decreased. This can be realized by use of the first scanning means of the particle beam irradiation apparatus. For example, in the case where a respiratory-movement target is the irradiation subject, the foregoing effect can make it possible that a three-dimensional dose distribution can be given to the target at higher accuracy.

A pseudo-enlargement spot, having the predetermined dose distribution 26, enlarged by the first scanning means 3 is scanned over and irradiated onto the target region 7, as illustrated in FIG. 1, by the second scanning means 4 provided at the downstream side of the first scanning means 3, in accordance with the second scanning pattern set in a treatment plan (unillustrated). On that occasion, the respective irradiation doses of pseudo-enlargement spots at the irradiation positions in the second scanning pattern are managed by the dose monitor 6; the irradiation control means performs the second scanning operation in such a way that the total dose of all the pseudo-enlargement spots 26 becomes equal to the dose distribution determined in the treatment plan. While the second scanning operation is carried out, the position of the pseudo-enlargement spot 26 is monitored by the position monitor 6 so as to be controlled.

After passing through the second scanning means 4, the charged particle beam 10 passes through the beam outlet window 5, enter the air from a vacuum region, and passes through the set 6 of a dose monitor and a beam position monitor; then, the charged particle beam 10 is irradiated onto the target region 7. The dose distribution of the spot of the charged particle beam 10 is enlarged by the first scanning means 3, so that the charged particle beam 10 becomes the pseudo-enlargement spot 26; the pseudo-enlargement spot 26 is scanned by the second scanning means 4 over arbitrary positions in the target region 7 and forms in the target region 7 a three-dimensional dose distribution determined in a treatment plan. In addition, although not illustrated, by use of a beam energy changing means for the charged particle beam 10, depth-direction positional scanning is performed in the target region 7.

According to the foregoing explanation, the scanning cyclic frequency f2 (although there exist X-direction and Y-direction ones, the faster scanning cyclic frequency is designated) of the second scanning means 4 is usually 10 Hz to 100 Hz; therefore, it is desirable that the scanning cyclic frequency f1 (although there exist X-direction and Y-direction ones, the slower scanning cyclic frequency is designated) of the first scanning means 3 is higher than several hundred hertz to several kilohertz. In general, the fact that, as the necessary deflection angle (proportional to the scanning width in the target region 7) of the scanning electromagnet becomes larger, the scanning speed (scanning cyclic frequency) is raised leads to upsizing of the driving power source for the scanning electromagnet. The necessary scanning width A2 for the second scanning means 4 is as large as the width of a tumor, i.e., several centimeters to several ten centimeters. In contrast, the necessary scanning width A1 for the first scanning means 3 is as large as the size of a pre-enlargement spot, i.e., smaller than several centimeters. Accordingly, because A1 is usually one-tenth of A2, it is relatively easy to make f1 higher than f2.

In comparison with the case where the first scanning means 3 is disposed at the downstream side of the second scanning means 4, in the case where the first scanning means 3 is disposed at the upstream side of the second scanning means 4 (not limited thereto), as illustrated in FIG. 1, the necessary magnetic-pole gap (a space through which the charged particle beam 10 passes) of the scanning electromagnet may be small when the first scanning means is configured with two dipole scanning electromagnets; therefore, there is demonstrated an effect that the scanning cyclic frequency f1 of the first scanning means can readily be raised. In the foregoing explanation, as the means for enlarging the original beam spot, only the first scanning means 3 has been utilized; however, in fact, in the case of a particle beam, such as a carbon beam, which scatters little in a target, it may be allowed that there is preliminarily inserted a scattering material of a constant thickness such that energy loss is negligible so that a slightly large pre-enlargement spot 21 is formed, and then the arbitrary-changeable first scanning means 3 rapidly changes the dose distribution of the pre-enlargement spots 21 to an arbitrary dose distribution.

The effect of the particle beam irradiation apparatus according to Embodiment 1 will be explained. The enlargement of the dose distribution of beam spots is realized by use of the first scanning means 3; therefore, unnecessary loss in the beam energy can be eliminated. In other words, in accordance with the first scanning pattern formed by the first scanning means 3, by use of the dose distribution of beam spots enlarged through high-speed and small-amplitude scanning operation, and by use of the second scanning means, the dose distribution of the enlarged beam spots is scanned and irradiated onto a diseased site, a necessary there-dimensional dose distribution can be formed; therefore, unnecessary loss in the energy of charged particle beam can be suppressed. Accordingly, there is demonstrated an effect that, compared with a conventional technology, a diseased site situated at deeper position can be irradiated by the particle beam acceleration means 1 having the same maximum exiting beam energy.

By appropriately setting operation parameters including the scanning patterns 24a, 24b, and 24c of the first scanning means 3, the formed pseudo-enlargement spots 26a, 26b, and 26c can form the dose distribution of spot that is larger than the pre-enlargement spot 21, while maintaining the 80%-to-20% width that is as wide as the pre-enlargement spot 21. Accordingly, the final dose distribution formed by scanning the pseudo-enlargement spots 26a, 26b, and 26c over the target region 7 with the second scanning means can be made similar to the penumbra of the pre-enlargement spot 21 in the border between the target region 6 and normal tissues in the vicinity thereof. In other words, the final dose distribution has a steeper dose distribution (small penumbra) than ever before. As a result, compared with conventional technology, any unnecessary dose given to a normal tissue can be reduced so that the therapy effect is raised.

Moreover, by changing operation parameters including the first scanning patterns 24a, 24b, and 24c of the first scanning means 3, it is made possible to rapidly change the dose distribution shape and the size of an enlarged beam spot in accordance with a control signal while scanning is performed; therefore, there can be formed a high-accuracy three-dimensional dose distribution even for a complex tumor shape. Furthermore, there can be realized a means, for rapidly changing the dose distribution of spots, that can reduce the number of changes in parameters for the beam transport system.

Next, with regard to the first scanning pattern, in FIGS. 6 and 7, there has been explained a case where the scanning pattern of the first scanning means 3 is approximately circular. However, because the objective of the first scanning means 3 is to enlarge, as maybe necessary (in accordance with the instruction of a treatment plan), the size of the charged particle beam 10 transported from the particle beam accelerator 1, the shape of the pseudo-enlargement spot 26 may not necessarily be circular. For example, as illustrated in FIGS. 8 and 9, it is also made possible that, by making the scanning pattern 24 of the first scanning means 3 to be a spiral orbit, there is eventually formed the pseudo-enlargement spot 26b whose middle portion is approximately flat, as represented in FIG. 9, and the 80%-to-20% width of the edge portion of which is as similar to the pre-enlargement spot 21 as possible. In this case, because there can be formed the pseudo-enlargement spot 26b that is further larger than the pseudo-enlargement spot represented in FIG. 7, there can be reduced the irradiation time of the second scanning means when irradiation is performed onto a large diseased site 7.

In the case represented in FIGS. 10 and 11, the scanning pattern 24c of the first scanning means 3 has the shape of a saw-tooth wave; through this, a rectangular pseudo-enlargement spot 26c, represented in FIG. 11, can be obtained. For example, there is demonstrated an effect that, even in the case where the target region 7 has a rectangular corner, as represented in FIG. 12, by scanning the rectangular pseudo-enlargement spot 26c (in FIG. 12, expressed as a rectangular spot 29) with the second scanning means 4, there can be formed a dose distribution whose shape is further similar to that of the target region 7. In other words, the first scanning means 3 for enlarging the spot size of the charged particle beam 10 can perform enlargement of a beam spot by calling up, in accordance with an irradiation control means, a plurality of arbitrary-shape first scanning patterns 3 preliminarily stored in a storage medium or the like of the irradiation control means.

To date, the size of a spot has been changed by inserting a scattering material into the beam path; therefore, it has not been realistic to change the size of a spot during irradiation of a beam, because it takes a considerable amount of time to move this scattering material mechanically. In contrast, according to Embodiment 1, by, in accordance with the shape of the target region 7, preliminarily determining which first scanning pattern 24 to use for each scanning potion of the second scanning means 4 in the stage of creating a treatment plan, it is made possible to rapidly change the size and the shape of a spot during irradiation. Accordingly, as represented in FIG. 12, it is made possible to selectively utilize plural kinds of pseudo-enlargement spots (small regions) 27, 28, 29, and the like. In a practical operation, by arranging these enlarged spots scanned by the second scanning means 4 in such a way that the distributions thereof sufficiently overlap with one another, it is made possible to optimize the position and the irradiation dose of each enlarged spot so that, as represented in FIG. 12, a necessary three-dimensional dose distribution is formed in the target region 7.

Moreover, as described already, a spot enlargement means can realize a dose distribution penumbra that is as small as the original spot size; therefore, even in the case where there exists the major organ 30 represented in FIG. 12, it is made possible to focus necessary dose on the target region 7 and to suppress the dose irradiated onto the major organ 30 at the minimum level. Actually, depending on the size of a diseased site, there exist several-hundred to several-hundred-thousand pseudo-enlargement spots that are scanned and irradiated by the second scanning means.

In Embodiment 1, there has been explained that the first scanning means 3 is configured with two scanning electromagnets whose scanning directions are perpendicular to each other; however, the first scanning means 3 may be configured with two scanning electromagnets formed of an air-core coil. Because the scanning width (scanning range) necessary for the first scanning means 3 is small, there can be obtained a sufficient scanning width even with an electromagnet formed of an air-core coil. Accordingly, there is demonstrated an effect that a further higher scanning cyclic frequency f1 can be realized. In order to realize excellent high-speed performance, scanning electromagnets utilizing a high-speed-response magnetic material or the like may be adopted as the two scanning electromagnets. For example, there may be formed a scanning electromagnet for the first scanning means 3 that can perform high-speed scanning, by combining a magnetic material, such as a ferrite core, having high-speed responsiveness and a coil.

Using a scanning electric field as the first scanning means 3 demonstrates the same effect described above. It may be allowed that, as the scanning power source for the first scanning means 3, a pattern power source or a resonance power source that vibrates at high speed is utilized. There may be utilized a power source that is driven by use of a random signal source that vibrates at high speed. The first scanning means 3 and the second scanning means 4 are arranged at the downstream side of the particle beam transport means 2 in the charged particle beam path, and the first scanning means 3 is disposed at the upstream side of the second scanning means 4; however, changing the order of arrangement of the first scanning means 3 and the second scanning means 4 demonstrates the same basic effect described above. Furthermore, even in the case where the first scanning means 3 and the second scanning means 4 are arranged in a nesting manner or at the same position, there can be obtained the same effect described above . In sum, the scanning cyclic frequency f1 of the first scanning means 3 should be higher than the scanning cyclic frequency f2 of the second scanning means 4, and the scanning width A1 of the first scanning means 3 should be smaller than the scanning width A2 of the second scanning means 4. Then, a stable enlarged spot can be obtained through the first scanning means 3.

It is preferable that the maximum scanning width A1 through the first scanning means 3 is the same as or smaller than one-third of the maximum scanning width A2 through the second scanning means 4 and the scanning cyclic frequency f1 of the first scanning means 3 is the same as or higher than three times the scanning cyclic frequency f2 of the second scanning means 4. It is more preferable that the ratio of f1 to f2 is not integer, in order to avoid an unnecessary synchronous phenomenon. Even in the case where the first scanning means 3 is configured in such a way as to form a pseudo-enlargement spot by superimposing a predetermined high-speed signal on electromagnets included in the particle beam transport means 2, there is demonstrated the same effect. In that case, it is not required to provide no electromagnet dedicated to the first scanning means 3; therefore, there can be obtained an effect that not only the particle beam irradiation apparatus can more simply be configured, but also the cost can be reduced.

The first scanning means may be configured by use of a deflection magnetic field or a deflection electric field generated by at least one electromagnet, permanent magnet, or deflection electrode. That is to say, the circular orbit scanning according to the scanning pattern 24a represented in FIG. 6 is realized by means of a rotating electric field or a rotating magnetic field. Of course, in order to form a smooth pseudo-enlargement spot 26, it is required to make the width of scanning through the magnetic field or the electric field to be as large as the size of the pre-enlargement spot 21. In that situation, the rotation speed per second corresponds to f1. In that situation, the same effect described above can be obtained.

Embodiment 2

Figure 2:
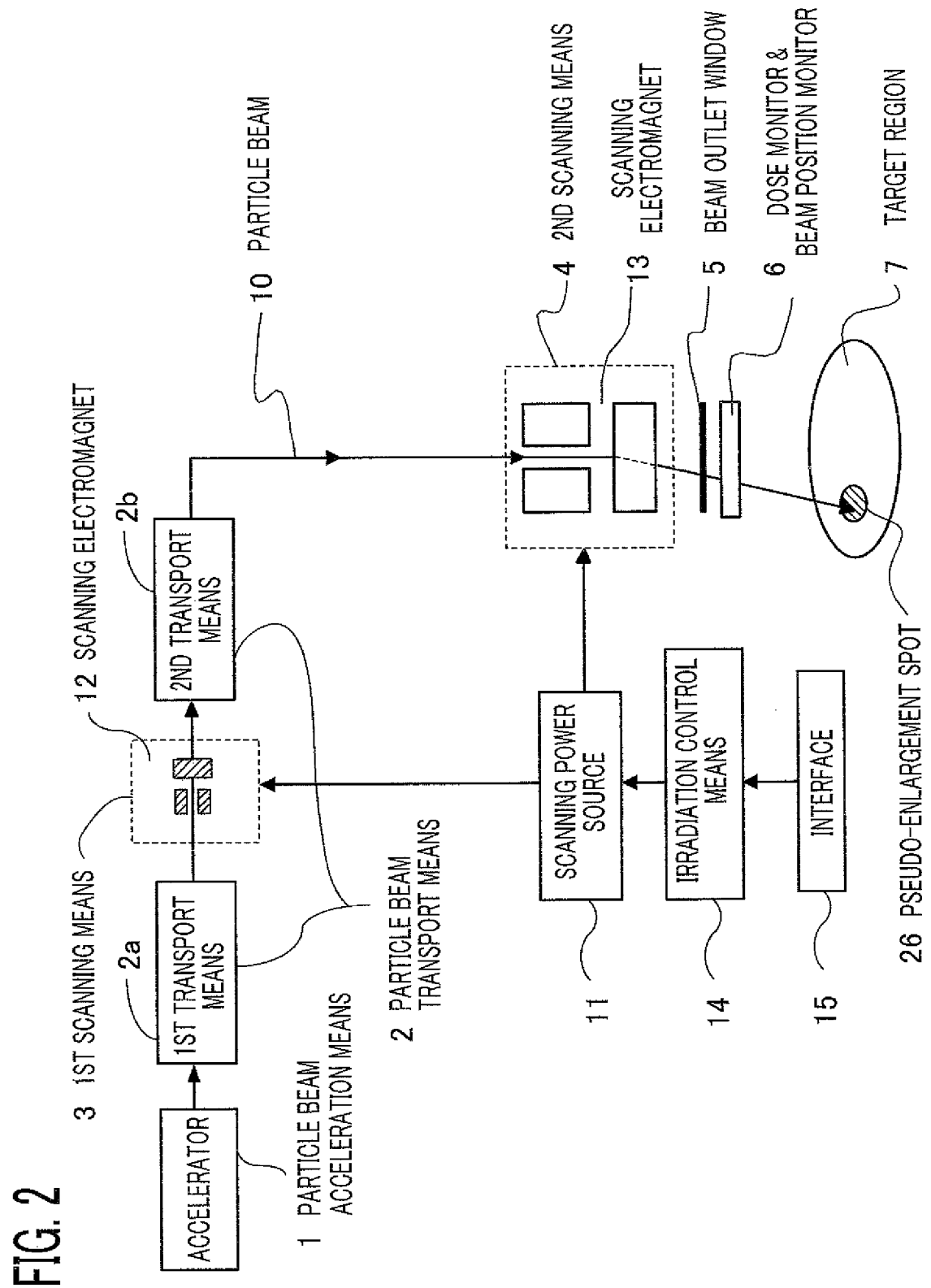
FIG. 2 is a configuration diagram illustrating a particle beam irradiation apparatus according to Embodiment 2.

FIG. 2 is a diagram for explaining the basic configuration and the operation of a particle beam irradiation apparatus (or a particle beam therapy system) according to Embodiment 2. In FIG. 2, the same reference numerals as those in FIG. 1 denote the same or equivalent elements. Reference numeral 2 denotes a particle beam transport means that has a first transport means 2a and a second transport means 2b. Reference numeral 3 denotes the first scanning means. What differs from FIG. 1 is that the first scanning means 3 is disposed at the downstream side of the particle beam acceleration means 1 and in the particle beam path of the particle beam transport means 2. The particle beam transport means 2 described here is usually referred to as an HEBT (High Energy Beam Transport System) and configured with a plurality of deflection electromagnets and focusing electromagnets. In general, when the first scanning means 3 is disposed at a position, in the HEBT system, that is separated from the target region 7 and is as upstream as possible, a large deflection distance (scanning width) can be obtained in the target region 7 even in the case where the deflection angle (kick angle) is small.

In this situation, the larger is the ratio of the deflection distance in the target region 7 to the deflection angle through the first scanning means 3, the less may be the required deflection angle (the amount of excitation) through the first scanning means 3; thus, the scanning speed (scanning cyclic frequency) of the first scanning means 3 can be raised. Accordingly, when, with regard to the arrangement position of the HEBT system, the first scanning means 3 is disposed at an arrangement position that is selected in such a way that the ratio of the deflection distance in the target region 7 to the deflection angle through the first scanning means 3 (deflection distance/deflection angle) is as large as possible, there can be obtained the first scanning pattern where the cyclic frequency f1 is higher. In practice, the first scanning means, which is to be disposed in the particle beam transport means, is disposed at a position where the ratio of the amount of a particle-beam-spot positional deviation in the target region, which is caused through a minute particle-beam deflection by the first scanning means to the amount of the minute deflection is larger than a required value.

Next, the operation of the particle beam irradiation apparatus according to Embodiment 2 will be explained. A charged particle beam 10 accelerated by the particle beam acceleration means 1 is transported to the irradiation system by way of a particle beam transport means 2; on that occasion, the charged particle beam 10 is scanned by the first scanning means 3 provided in the path of the particle beam transport means 2, with a minute amplitude (scanning width) and at high speed, so that a pseudo-enlargement spot 26 can be formed in the target region 7. The pseudo-enlargement spots 26 are controlled by the first scanning means 3 so that there is formed a dose distribution, of pseudo-enlargement spots, which corresponds to a pattern selected from a plurality of preliminarily stored first scanning patterns. Accordingly, for example, by transmitting a command to the first scanning means 3 through the interface 15, the dose distribution of the pseudo-enlargement spots 26 can rapidly be changed. In this case, unlike Patent Document 2, it is not required to change any of the setting values for all the electromagnets in the HEBT system. Unlike Patent Document 1, it is not required to insert a scattering material into the path of the charged particle beam 10. The spots 26 enlarged in such a way as to have a predetermined dose distribution are scanned, in the target region 7, by the second scanning means 4 controlled by the irradiation control means in accordance with a treatment plan, so that there is formed a three-dimensional dose distribution that coincides with the target region 7.

The depth-direction scanning in the target region 7 is performed by changing the beam energy of the charged particle beam 10. As the changing methods, there exist two methods, i.e., a method of directly changing the energy of a beam exiting from the particle beam acceleration means 1 and a method of inserting a range shifter into the path of a charged particle beam. In the particle beam irradiation apparatus according to Embodiment 2, in addition to the effect described in Embodiment 1, there is demonstrated another effect that the required deflection angle of the first scanning means 3 can be reduced, by providing the first scanning means 3 at a desirable position in the HEBT system. As a result, not only the scanning speed (scanning cyclic frequency) f1 of the first scanning means 3 can simply be raised, but also the cost of the scanning power source for the first scanning means 3 can be reduced.

There may be provided a plurality of first scanning means 3 at a plurality of positions in the HEBT system and the irradiation system. In that case, by turning on or off the first scanning means 3 provided at the foregoing positions, switching the first scanning patterns can be performed. There is demonstrated an effect that the switching the first scanning patterns can more simply and more securely be performed.

Embodiment 3

FIG. 14 is a set of charts representing the dose distribution of pre-enlargement spots obtained from the accelerator and the shape thereof. FIG. 15 is a set of charts representing a dose distribution of pseudo-enlargement spots and the shape thereof according to Embodiment 3; in FIGS. 14 and 15, reference numeral 34 denotes a dose distribution of pre-enlargement spots obtained from the accelerator 1; reference 34a denotes the shape thereof. Reference numeral 35 denotes a dose distribution of pseudo-enlargement spots; reference numeral 35a denotes the shape of a pseudo-enlargement spot. In some cases, as the particle-beam source, a synchrotron accelerator is utilized in a particle beam irradiation apparatus. In general, the shape of a charged particle beam extracted from the synchrotron accelerator is asymmetric on the X-Y plane. For example, the charged particle beam has an asymmetric cross-sectional shape that is extended in the Y direction, as represented in FIG. 14(b). In the case where this kind of asymmetric beam is introduced into a rotating gantry irradiation apparatus (not illustrated) or the like, there is caused a phenomenon in which, in an irradiation subject, the shape represented in FIG. 14(b) rotates in accordance with the rotation angle of the rotating gantry.

Thus, in terms of simplifying the irradiation procedure and raising the irradiation accuracy, it is important to make the shape of the dose distribution of pre-enlargement spots obtained from the accelerator 1 as symmetric as possible. It is made possible that the asymmetric pre-enlargement spot 34a obtained from the accelerator 1 is scanned by the first scanning means 3 in the X direction in accordance with a predetermined scanning pattern and eventually the distribution in the X direction is widened. By adjusting the detailed pattern and range of scanning, it is made possible to make the dose distribution 35 and the shapes 35a of pseudo-enlargement spots more symmetric, as represented in FIG. 15. As a specific example, assuming that the scanning speed in the X direction is V(x), in the case where V(x), as a function of the amount of scanning x, is made low at positions where x is approximately equal to zero and made to become higher as the absolute value of x becomes larger, the distribution of spots in the X direction can be widened. For example, the reciprocal of the Gaussian distribution is adopted as V(X). As a result, even in a particle beam irradiation apparatus utilizing a rotating gantry, the shape of a pseudo-enlargement spot irradiated onto an irradiation position can be made approximately constant even when the rotation angle of the rotating gantry changes; therefore, there is demonstrated an effect that the accuracy of scanning irradiation can be raised.

Embodiment 4

A particle beam irradiation apparatus according to Embodiment 4 will be explained. In Embodiment 4, a plurality of scanning modes is prepared in accordance with plural kinds of dose distributions of pseudo-enlargement spots formed by the first scanning means. In the irradiation control means (scanning irradiation control means), an interface, which can be operated by an operator, is prepared so that the operator can select, through this interface, a scanning pattern and scanning mode that are actually utilized in performing irradiation. In such a manner as described above, there can be performed scanning irradiation in which there is utilized the distribution, of pseudo-enlargement spots, which is preliminarily determined in a treatment plan in accordance with the conditions of a target region to be irradiated.

As a result, in the case where, as described in Embodiment 1 and 2, it is not required to concurrently utilize a plurality of pseudo-enlargement spots during a single irradiation, there is demonstrated an effect that scanning irradiation can simply and securely be performed by use of a predetermined scanning mode. The first scanning means can scan a charged particle beam obtained from the accelerator in one-dimension or two-dimension. The scanning pattern through the first scanning means is effective when a high-speed scanning signal or a white noise scanning signal is utilized in such a way that the distribution of pseudo-enlargement spots utilized in the second scanning means changes sufficiently less than the distribution of beam currents in the accelerator changes due to temporal structure. In principle, in the case where the white noise scanning signal is utilized, beam spots is uniformly distributed in the scanning range of the first scanning means; therefore, because the beam spots are insusceptible to temporal change in the beam current, there can be obtained pseudo-enlargement spots having a stable distribution (the distribution per se is not necessarily uniform). As a result, a high-accuracy scanning irradiation dose distribution can be obtained.

Embodiment 5

FIG. 16 is a configuration diagram illustrating a particle beam irradiation apparatus according to Embodiment 5. Each of the irradiation control means 14 and the scanning power source 11 illustrated in FIG. 1 maybe configured in such a way as to be separated as illustrated in FIG. 16. An irradiation control means 14 is provided with a first irradiation control means 14a that outputs an enlarged spot forming signal for scanning a charged particle beam so as to form a pseudo-enlargement spot ; and a second irradiation control means 14b that outputs an enlarged spot scanning signal for making the position of a pseudo-enlargement spot coincide with the target region and performing scanning. In the scanning power source 11, there is provided a first scanning power source 11a that receives the output from the first irradiation control means 14a and then scans the first scanning means 3. Furthermore, in the scanning power source 11, there is provided a second scanning power source 11b that receives the output from the second irradiation control means 14b and then scans the second scanning means 4. By, as described above, separating the irradiation control means 14 and the scanning power source 11 for the first scanning means 3 and the second scanning means 4, control can readily be performed, whereby the electric power and frequency of the scanning power source can easily be controlled.

Embodiment 6

The roles, disclosed in the present invention, of the first scanning means for forming a pseudo-enlargement spot and the second scanning means for scanning a pseudo-enlargement spot maybe realized by a scanning apparatus 16 (refer to FIG. 17), which is a set of X-direction and Y-direction scanning electromagnets 17. The scanning apparatus 16 can perform two-dimensional scanning in directions that are perpendicular to the traveling direction of a charged particle beam. FIG. 17 is a configuration diagram illustrating a particle beam irradiation apparatus according to Embodiment 6. The irradiation control means 14 is provided with the first irradiation control means 14a that outputs an enlarged spot forming signal for scanning a charged particle beam so as to form a pseudo-enlargement spot; and the second irradiation control means 14b that outputs an enlarged spot scanning signal for making the position of a pseudo-enlargement spot coincide with the target region and performing scanning. The scanning power source 11 is provided with the first scanning power source 11a that receives the output from the first irradiation control means 14a and the second scanning power source 11b that receives the output from the second irradiation control means 14b. The enlarged spot forming signal from the first scanning power source 11a and the enlarged spot scanning signal from the second scanning power source 11b are superimposed on each other by an adder 18 and then outputted to the scanning apparatus 16. In other words, a signal obtained by superimposing the enlarged spot forming signal on the enlarged spot scanning signal is outputted to the scanning apparatus 16. By, as described above, separating the scanning power source 11, the electric power and the frequency of the scanning power source is controlled easily.

Figure 18:
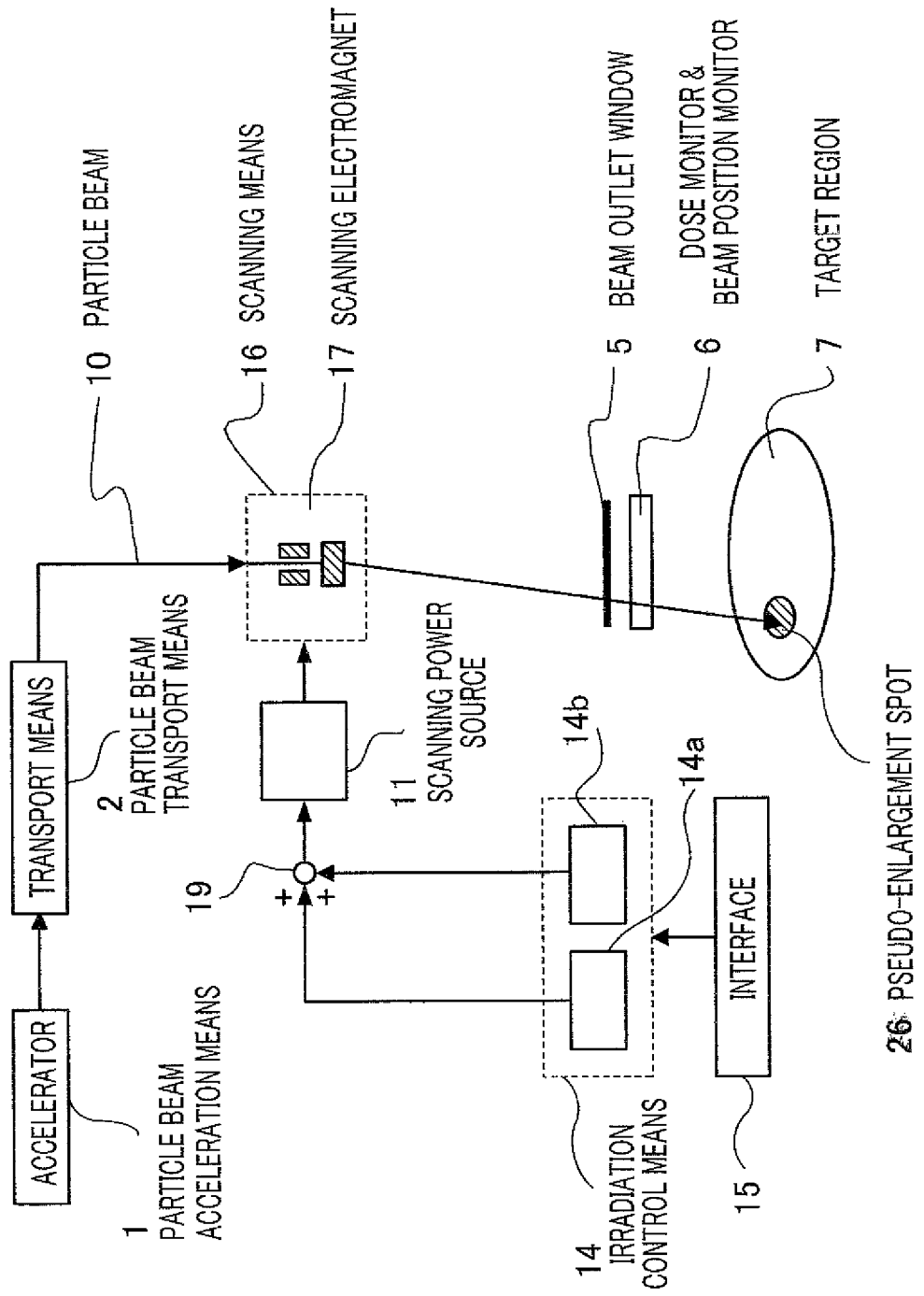
FIG. 18 is a configuration diagram illustrating another particle beam irradiation apparatus according to Embodiment 6.

FIG. 18 is a configuration diagram illustrating another particle beam irradiation apparatus according to Embodiment 6. As is the case with FIG. 17, only a single scanning apparatus 16 is utilized. The enlarged spot forming signal outputted from the first irradiation control means 14a and the enlarged spot scanning signal from the second irradiation control means 14b are superimposed on each other by an adder 19 and outputted to the scanning apparatus 16 byway of the scanning power source 11; then, the scanning apparatus 16 is controlled. In Embodiment 6, a single irradiation apparatus 16 is utilized; therefore, the configuration is simple.

Also in Embodiment 6, in order to form the predetermined second scanning pattern in the target region 7 represented in FIG. 12, it may be allowed that each of the pseudo-enlargement spots (i.e., the small spot, the large spot, and the quadrangular spot) is formed through continuous scanning by the first scanning means 16, and that the predetermined second scanning pattern is formed through continuous scanning (raster scanning), discontinuous (spot scanning), or continuity-discontinuity mixed scanning (hybrid scanning) by the second scanning means 16. In other words, it may be allowed that, after outputting the enlarged spot forming signal for scanning a charged particle beam so as to form a pseudo-enlargement spot, the irradiation control means outputs the enlarged spot scanning signal for making the position of the pseudo-enlargement spot coincide with the target region and then performing scanning. It may also be allowed that, while outputting the enlarged spot forming signal for scanning a charged particle beam so as to form a pseudo-enlargement spot, the irradiation control means outputs the enlarged spot scanning signal for making the position of the pseudo-enlargement spot coincide with the target region and then performing scanning.

The invention claimed is:

1. A particle beam irradiation apparatus comprising:
   a particle beam acceleration means that accelerates a charged particle beam;
   a particle beam transport means that transports a charged particle beam launched from the particle beam acceleration means;

a scanning apparatus that includes a first scanning means and a second scanning means, each of said first and second scanning means being configured to (i) generate a deflection magnetic field or a deflection electric field in a direction that is perpendicular to a traveling direction of the charged particle beam, and (ii) two-dimensionally scan the charged particle beam transported by the particle beam transport means; and an irradiation control means configured to:
(i) control the first scanning means to scan the charged particle beam in two dimensions to irradiate a small region of a target region, such that the first scanning means performs scanning of the small region of the target region cyclically with a scanning pattern to administer a predetermined dose distribution of irradiation to the small region, and
(ii) control the second scanning means to move the small region scanned by the first scanning means to different areas of the target region, wherein the small regions scanned by the first scanning means in the different areas have portions overlapped with one another.

2. The particle beam irradiation apparatus according to claim 1, wherein the irradiation control means further controls the first scanning means so that its maximum scanning width is smaller than the maximum scanning width by the second scanning means.

3. The particle beam irradiation apparatus according to claim 1, wherein the irradiation control means controls the first scanning means so as to two-dimensionally scan the charged particle beam over the small region serving as the irradiation subject, and then controls the second scanning means so as to change the small region serving as the irradiation subject to be a different small region among the plurality of the small regions.

4. The particle beam irradiation apparatus according to claim 1, wherein the irradiation control means controls the first scanning means so as to two-dimensionally scan the charged particle beam over the small region serving as the irradiation subject, and also controls the second scanning means so as to change the small region serving as the irradiation subject to be a different small region among the plurality of the small regions.

5. The particle beam irradiation apparatus according to claim 1, wherein the first scanning means is disposed at an upstream side of the second scanning means in a path of a charged particle beam.

6. The particle beam irradiation apparatus according to claim 5, wherein the first scanning means and the second scanning means are arranged at a downstream side of the particle beam transport means in the path of a charged particle beam.

7. The particle beam irradiation apparatus according to claim 1, wherein the first scanning means is disposed in a path of a charged particle beam within the particle beam transport means.

8. The particle beam irradiation apparatus according to claim 1, wherein the first scanning means is formed of electromagnets included in the particle beam transport means.

9. The particle beam irradiation apparatus according to claim 1, wherein a plurality of the first scanning means is disposed in a path of a charged particle beam, and one or more of the plurality of the first scanning means is selected to operate.

10. The particle beam irradiation apparatus according to claim 1, wherein the irradiation control means includes an interface configured to be operated by an operator for (i) inputting a command to the irradiation control means, (ii) selecting a plurality of scanning patterns or scanning modes in which the plurality of the small regions is scanned by the first scanning means, and (iii) inputting the selected scanning patterns or scanning modes to the irradiation control means.

11. The particle beam irradiation apparatus according to claim 1, wherein the interface can specify a shape and a size of the plurality of the small regions.

12. A particle beam irradiation apparatus comprising:
a particle beam acceleration means that accelerates a charged particle beam;
a particle beam transport means that transports a charged particle beam launched from the particle beam acceleration means;
a scanning apparatus that generates a deflection magnetic field or a deflection electric field in directions that are perpendicular to a traveling direction of the charged particle beam, and two-dimensionally scans the charged particle beam transported by the particle beam transport means; and
an irradiation control means configured to
(i) output to the irradiation apparatus a first control signal for controlling the scanning apparatus to scan the charged particle beam in two dimensions to irradiate a small region of a target region, such that the scanning performs scanning of the small region of the target region cyclically with a scanning pattern to administer a predetermined dose distribution of irradiation to the small region, and
(ii) output a second control signal for controlling the scanning apparatus to move the small region scanned, in response to the first control signal, to different areas of the target region, wherein the small regions scanned, in response to the first control signal, have portions overlapped with one another.

13. The particle beam irradiation apparatus according to claim 12, wherein the irradiation control means outputs the first control signal, and then outputs the second control signal.

14. The particle beam irradiation apparatus according to claim 12, wherein the irradiation control means outputs the first control signal, and also outputs the second control signal.

15. A particle beam irradiation apparatus comprising:
a particle beam acceleration means that accelerates a charged particle beam;
a particle beam transport means that transports a charged particle beam launched from the particle beam acceleration means;
a scanning apparatus that includes a first scanning means and a second scanning means, each of said first and second scanning means being configured to (i) generate a deflection magnetic field or a deflection electric field in a direction that is perpendicular to a traveling direction of the charged particle beam, and (ii) two-dimensionally scan the charged particle beam transported by the particle beam transport means; and an irradiation control means configured to:
(i) control the first scanning means to scan the charged particle beam in two dimensions to irradiate a small region of a target region, such that the first scanning means performs scanning of the small region of the target region cyclically with a scanning pattern to administer a predetermined dose distribution of irradiation to the small region, and
(ii) control the second scanning means to move the small region scanned by the first scanning means to different areas of the target region, wherein the small regions scanned by the first scanning means in the different areas have portions overlapped with one another, and (iii) controls the scanning apparatus so that the scanning speed the first scanning means is faster than the movement speed of the second scanning means.

16. The particle beam irradiation apparatus according to claim 15, wherein the irradiation control means controls the scanning apparatus so that the maximum scanning width by the first scanning means is smaller than the maximum scanning width by the second scanning means.

17. The particle beam irradiation apparatus according to claim 15, wherein the first scanning means is disposed in a path of a charged particle beam within the particle beam transport means.

18. The particle beam irradiation apparatus according to claim 15, wherein the irradiation control means includes an interface configured to be operated by an operator for (i) inputting a command to the irradiation control means, (ii) selecting a plurality of scanning patterns or scanning modes in which the plurality of the small regions is scanned by the first scanning means, and (iii) inputting the selected scanning patterns or scanning modes to the irradiation control means.

19. A particle beam irradiation apparatus comprising:
- a particle beam acceleration means that accelerates a charged particle beam;
- a particle beam transport means that transports a charged particle beam launched from the particle beam acceleration means;
- a scanning apparatus that scans a charged particle beam transported by the particle beam transport means; and
- an irradiation control means configured to
- (i) output to the irradiation apparatus a first control signal for controlling the scanning apparatus to scan the charged particle beam in two dimensions to irradiate a small region of a target region, such that the scanning performs scanning of the small region of the target region cyclically with a scanning pattern to administer a predetermined dose distribution of irradiation to the small region, and
- (ii) output a second control signal for controlling the scanning apparatus to move the small region scanned, in response to the first control signal, to different areas of the target region, wherein the small regions scanned, in response to the first control signal, have portions overlapped with one another; and
- the scanning speed of the charged particle beam controlled by the first control signal is faster than the movement speed of the small region controlled by the second control signal.

* * * * *